United States Patent [19]

Bacus

[11] Patent Number: 5,202,931
[45] Date of Patent: Apr. 13, 1993

[54] METHODS AND APPARATUS FOR THE QUANTITATION OF NUCLEAR PROTEIN

[75] Inventor: James W. Bacus, Hinsdale, Ill.

[73] Assignee: Cell Analysis Systems, Inc., Lombard, Ill.

[21] Appl. No.: 902,504

[22] Filed: Jun. 23, 1992

Related U.S. Application Data

[60] Continuation of Ser. No. 809,229, Dec. 17, 1991, abandoned, which is a continuation of Ser. No. 628,483, Dec. 14, 1990, abandoned, which is a division of Ser. No. 106,717, Oct. 6, 1987, Pat. No. 5,008,185.

[51] Int. Cl.$^5$ .............................................. G06K 9/00
[52] U.S. Cl. ...................................................... 382/6
[58] Field of Search ...................... 435/7.23, 7.1, 960; 436/46, 64, 86, 501, 503, 813; 364/413.13–413.22, 413.01; 382/6

[56] References Cited

U.S. PATENT DOCUMENTS

| | | | |
|---|---|---|---|
| 4,307,376 | 12/1981 | Miller et al. | 382/6 |
| 4,345,027 | 8/1982 | Dolbeare | 435/21 |
| 4,741,043 | 4/1988 | Bacus | 382/6 |
| 4,812,412 | 3/1989 | Turner | 436/15 |
| 4,845,552 | 7/1989 | Jaggi et al. | 382/6 |
| 4,998,284 | 3/1991 | Bacus et al. | 382/6 |
| 5,016,283 | 5/1991 | Bacus et al. | 382/6 |
| 5,018,209 | 5/1991 | Bacus | 382/6 |
| 5,046,108 | 9/1991 | Inoue et al. | 382/6 |

FOREIGN PATENT DOCUMENTS

| | | |
|---|---|---|
| WO8301779 | 5/1983 | European Pat. Off. . |
| 0204992 | 12/1986 | European Pat. Off. . |
| WO8702802 | 5/1987 | European Pat. Off. . |
| WO8702803 | 5/1987 | European Pat. Off. . |
| WO8706705 | 11/1987 | European Pat. Off. . |
| 2019778 | 2/1973 | Fed. Rep. of Germany . |

OTHER PUBLICATIONS

Tucker, J. et al., Clinical Cytometry and Histochemistry, pp. 403–406.
Int. J. of Gynecol. Pathol., vol. 5, No. 2, 199–131, 1986, C. Charpin, et al.
Cytometry, vol. 7, No. 4, 1986, pp. 325–330, Oud, et al.
Histochemistry, vol. 85, 1986, pp. 139–143, G. Harms, et al.
The Microscope, vol. 24, 1976, pp. 39–44, H. Aus, et al.
(List continued on next page.)

*Primary Examiner*—Stephen Brinich
*Attorney, Agent, or Firm*—Fitch, Even, Tabin & Flannery

[57] ABSTRACT

An image analysis system is used for the quantitation of nuclear proteins in cell populations. Particularly, the hormonal receptor content of fine needle aspirates of human breast carcinomas are evaluated. Estrogen or progesterone receptors are amplified and visualized in the specimen by a staining technique of the immunoperoxidase type. Monoclonal antibodies specific against the receptor are attached to the receptor sites and are then amplified by a bridging antibody which attaches to the monoclonal antibody and a peroxidase-antiperoxidase complex. A chromagen, diaminobenzidine is combined with the complex and treated with hydrogen peroxide to react with the peroxidase forming an insoluble brown precipitate which marks the receptor sites for optical identification. The specimen is then counterstained with another chromagen, methyl green which is specific to the nucleus of each cell. Two monochromatic filterings optically separate the areas stained by the receptor site optical enhancer and the nuclear area optical enhancer. Measurements of the optical density values of the stained receptor areas yield an intensity value directly related to the quantity of hormonal receptor in the specimen. A comparison of the nuclear area containing hormonal receptor with the total nuclear area yields a percentage value which indicates the distribution of cells throughout of the specimen which contain receptor. These two values for intensity and distribution are then combined to yield a predictive score for an assay. The measured score when compared to an empirically derived reference score is predictive of the prognosis of endocrine therapy.

25 Claims, 10 Drawing Sheets

OTHER PUBLICATIONS

Histochemistry, vol. 80, 1984, pp. 49–57, P. S. Oud, et al.
Am. J. Pathol., vol. 123, No. 2, 1986, pp. 280–292, Press, et al.
Proc. Natl. Acad. Sci. U.S.A., vol. 82, 1985, pp. 4803–4807, Shimada, et al.
J. Histochemistry and Cytochemistry, vol. 35, No. 11, pp. 1253–1259, 1987, Sklarew, et al.
Applied Optics, vol. 26, No. 16, 15 Aug., 1987, pp. 3280–3293, J. W. Bacus, et al.
Auer, et al., Analytical and Quantitative Cytology, 1982.
Auffermann, et al., Int. Acad. of Cytology, 1985.
Aufferman, et al., Analyt. & Quant. Cytology, 1984.
G. Brugal, Meth. and Achiev. in Exp. Pathology, vol. 11, pp. 1–33.
Abbott Laboratories ADC-500 Analyzer Brochure.
Longmore, et al., Analyt. and Quant. Cytology, vol. 4, No. 1, 1982, pp. 33–38.
Oud, et al., Analyt. and Quant. Cytology, vol. 3, No. 4, 1981, pp. 289–294.
Tucker, et al., Clinical Cytometry and Histometry, 1987, pp. 403–406.
Cancer Research, vol. 46, pp. 4271s–4277s, 1986, Charpin, et al.
Al, et al., J. of Histochemistry and Cytochemistry, vol. 27, No. 1, pp. 629–634, 1979.
Al, et al., In the Automation of Cancer Cytology Specimens and Cell Image Analysis, by Pressman, pp. 237–243, 1979.
Allison, et al., J. of Histochem. and Cytochem., vol. 29, No. 10, pp. 1219–1228.
Beyer–Boon, et al., In the Automation of Cancer Cytology Specimens and Cell Image Analysis, by Pressman, pp. 207–211, 1979.
Ploem–Zaaiejer, et al., In the Automation of Cancer Cytology Specimens and Cell Image Analysis, by Pressman, pp. 225–235, 1979.
Vander Ploeg, et al., Histochemistry, vol. 62, pp. 29–34, 1979.
Van Ingen, et al., In the Automation of Cancer Cytology Specimens and Cell Image Analysis, by Pressman, pp. 221–224, 1979.
Young, et al., IEEE Transactions of Biomedical Engineering, vol. BME-22, No. 1, 1975.
Seigneurin, et al., Analyt. and Quant. Cytology, vol. 6, No. 3, Sep., 1984.
Brugal, et al., Analyt. and Quant. Cytology and Histology, vol. 8, No. 3, Sep., 1986.
Brugal, et al., Roux's Arch. Dev. Biol., vol. 194, pp. 148–154, 1985.
Moustafa, et al., Roux's Arch. Dev. Biol., vol. 193, pp. 139–148, 1984.
Brugal, et al., Innov. Tech. Biol. Med., vol. 5, No. 3, 1984.
Brugal, et al., Techniques et Science Informatiques, vol. 4, No. 3, 1985.
Brugal, et al., Detection of Bladder Cancers Using a SAMBA 200 Cell Image Processor.

METHODS AND APPARATUS FOR THE QUANTITATION OF NUCLEAR PROTEIN

This application is a continuation of application Ser. No. 07/809,229 filed Dec. 17, 1991, now abandoned.

This application is a continuation of application Ser. No. 07/628,483 filed Dec. 14, 1990, now abandoned which is a division of application Ser. No. 07/106,717, filed Oct. 6, 1987 now U.S. Pat. No. 5,008,185.

The invention pertains generally to methods and apparatus for the quantitation of nuclear proteins, and is more particularly directed to the quantitative assay of nuclear material by image analysis which can be visualized with image enhancement factors specific to the protein under assay, such as monoclonal antibodies against the estrogen and progesterone receptors of carcinomas, specifically identifiable types of human breast cancers, or the like, bound to a peroxidase-antiperoxidase complex.

Nuclear proteins are of considerable interest in the medical field today. Their identification and the mapping of their structure are not only providing a view into the inner workings of cells, and possibly life itself, but are also useful in exploring the development and cure of particular pathologies. One of the more promising areas which will greatly benefit mankind is the research being done in nuclear protein analysis in relation to human carcinomas.

Specifically, it has been estimated that one out of every eleven women in the United States will develop some type of breast cancer in her lifetime. In spite of major advances during the last decade in chemotherapy and hormonal therapy for these diseases, the death rate from such disease has remained substantially the same. It is strongly suggested that further characterization and quantitation of the cancer cells responsible for these diseases is necessary to provide better and new methods of treatment.

It has long been known that some human breast cancers are hormone-dependent, such that they undergo striking regression when deprived of a supporting hormone by removal of the ovaries, adrenals, or pituitary; or an altering the hormonal milieu by the administration of androgens, large doses of estrogen, or antiestrogens such as tamoxifen. For those patients who respond, endocrine manipulation by either ablative or additive means may represent the best treatment now available for advanced breast cancer. However, only 25-30% of cancer patients have breast tumors of the hormone-dependent type. There has been a need for a means to distinguish those individuals who are favorable candidates for endocrine therapy, from the larger group whose breast cancers are unresponsive to hormonal treatment and who should be placed directly in chemotherapy.

Researchers have found that breast cancers showing low estrogen binding levels or lacking cytosolic estrogen receptor rarely respond to endocrine therapy, whereas most but not all patients with receptor containing tumors receive objective benefit from endocrine treatment. As the sensitivity of methods for the detection and estimation of estrophilin has improved, it has become apparent that some cancers thought to lack receptors actually contain very low levels of this protein. However, these tumors do not respond to endocrine therapy and should be classified with those totally lacking receptor. Therefore, the qualitative classification of "receptor-positive" or "receptor-negative" for tumors must be replaced with quantitative terms such as "receptor-rich" or "receptor poor" to predict favorable results, with the dividing line determined empirically. More recently, researchers have discovered that progesterone levels in tumors provide similar indications to those of estrogen levels. There remains the problem of accurately and reproducibly quantitating estrogen and progesterone receptor levels from tissue samples to determine where a tumor should be classified.

To be able to accurately quantify the estrogen receptor content in a tissue it has in the past been necessary to perform a biochemical assay on the tissue sample. One of the most used methods is the sucrose density gradient configuration as described by Jensen, et al. "Hormone Dependency in Breast Cancer" J. Steroid Biochem. 7:911-917, 1976. Biochemical assays have the problem of being extremely complex, time consuming, and expensive to accomplish along with the problem that they are not generally done at the same institution which makes a biopsy of the tumor.

Such biochemical assays also must use relatively large amounts of tissue and they consume the tissue sample. Additionally, biochemical assays can differ inexplicably between samples of the same tumor. While it is believed this may be due to the heterogeneity of the tissue samples, even in a single tumor there is no sure way to separate different features because a biochemical assay averages the estrogen receptor content over all the cellular material assayed. A sample with a mix of tumor cells and regular cells will be represented quite differently than a sample with all tumor cells, even though both samples really contain the same estrogen receptor content.

To partially overcome some of these difficulties, others in the art have sought to provide histochemical methods for the visualization of the content of estrogen receptors in a specimen by tagging the receptors with markers which can then be measured independently. Researchers have used radiolabeled estrogen, fluorescent estrogens, and conjugated anti-estradiol antibodies which are only relatively specific to the receptors. These tags can then be visualized by radiating the tissue sample with the correct beam energy such as X-rays or a particular frequency of light. Generally, these attempts at histochemical localization of estrogen receptor with anti-steroid antibodies or fluoresceinated estrogens have not yielded acceptable sensitivities and specificities when compared to the previous biochemical assays.

A newer immunohistochemical technique with much greater promise has been developed as a staining technique using a peroxidase-antiperoxidase complex, see King et al., "Comparison of Immunocytochemical and Steroid-Binding Assays for Estrogen Receptor in Human Breast Tumors" Cancer Research, V45, pgs. 293-304, January 1985. The method comprises utilizing a highly specific monoclonal antibody directed against the estrogen receptor protein. Such monoclonal antibodies developed specifically against estrogen receptor include those first characterized at the University of Chicago and designated H222 sP2 and H226 sP2. The principal advantages of this approach over the fluorescein-tagged ligands and radioisotope localization are the availability of well-characterized reagents and a sensitive immunoperoxidase technique for amplification and detection of the small amounts of receptor molecules present in a tissue sample.

The advantages of the PAP staining technique over a biochemical assay are greater, in that only a small tissue sample need be used and such samples can be taken from a patient through a fine needle aspiration. Thus, the immunocytochemical assay can be accomplished on tumors too small to yield sufficient material for biochemical assays. Because the individual cells of the specimen are visualized, heterogeneity in tissue samples can be dealt with adequately. In general, the immunocytochemical assays are simpler, less expensive, and more accurate than conventional biochemical assays.

Another reason for the difficulty in producing quantitative results which can be duplicated relates to the substantial lability of the estrogen receptor to partial or complete loss of its ability to bind estrogen under very mild conditions. There is reason to believe that the antigenic site of the receptor may be more stable to degradation than it is to binding activity. Thus, the immunohistochemical technique which can be accomplished shortly after an excision or biopsy has been made is preferable to the usual delay before a biochemical assay can be run.

For a researcher to determine the estrogen receptor content with the new immunohistochemical method, he views a stained tissue sample through a microscope and makes a subjective visual determination of the amount of staining for each cell. A weighted average of the observed cell staining is then used to form an opinion whether the specimen is receptor rich or receptor poor. This method provides but a qualitative, or at best a semi-quantitative, immunohistochemical technique for the assessment of estrogen receptor status in human breast cancers.

The data obtained by this method does indicate a significant correlation between immunohistochemical assays and quantitative biochemical assays, see McCarty, Jr. et al., "Estrogen Receptor Analysis", Arch Pathol Lab Med, Vol 109, August 1985. One researcher, Pertschuk, reported the results of 43 patients and McCarty Jr. et al. reported the results of 23 patients with metastatic breast carcinoma who were treated with hormonal therapy. The positive predictive value of the immunocytochemical assay in these patients was 85% and the negative predictive value was 91%. The corresponding values for conventional steroid-binding assays in these cases was 69% and 79%, respectively. In this limited number of patients, the immunocytochemical assay had a stronger correlation to the response to endocrine manipulative management than did the conventional steroid-binding assays.

However, the remaining problem of immunohistochemical assays relative to conventional methods is the lack of an accurate and reproducible quantitative assay at the cellular level. It is believed the development of a true quantitative assay at the cellular level using the immunohistochemical technique may further raise the positive predictive nature of the assay as a prognosis of endocrine therapy.

SUMMARY OF THE INVENTION

The invention provides methods and apparatus for the measurement of the quantity of specific nuclear proteins in a cellular population. One preferred method includes the utilization of computerized image analysis to determine from a digital grey scale image of a cell population the quantity of a particular protein. The grey scale image is representative of the amount of an optical enhancement factor, such as a chromogen, which binds to an equivalent amount of the specific protein under study and thereby allows optical amplification and visualization of the protein.

The apparatus includes a means for magnifying and displaying an image of a group of cells of a specimen from a field on a microscope slide. The specimen cell population is prepared with a special staining and counterstaining technique. After staining, the image field is digitized by the apparatus and stored in a memory provided by the apparatus. From the digitized image, a nuclear image mask is formed by filtering the image at one wavelength of light. The nuclear mask is stored and a second filter is used to form another filtered image of the areas with the optical enhancement factor. Differentiation of cellular characteristics can be made by comparing the first image with the second to obtain a quantitation of material stained with the optical enhancement factor and thus, an assay of the amount of the particular nuclear protein which is under study.

In a preferred embodiment, the invention is used to assay the tumor specimens of human breast cancers for hormonal receptor content, particularly estrogen and progesterone receptors. The estrogen and progesterone receptor content of breast carcinomas have been shown to provide clinically useful data in the medical management of patients with breast cancers. Endocrine manipulative management techniques can use the measured levels as predictors of the favorable use of these therapies.

Moreover, the methods of the invention for providing quantitative immunohistochemical assays for estrogen and progesterone receptor content can be applied to quantitative assays of other nuclear proteins, especially oncongene protein products (c-myb, c-myc, n-myc, c-fos), at least one of which (n-myc) has already been clinically shown to be important in determining the prognosis of neuroblastoma and retinoblastoma.

For estrogen receptor assays, specimens are prepared using a counterstaining technique where in a first step, the specimen is stained using an immunoperoxidase staining technique, the peroxidase technique including the use of a monoclonal antibody to estrophilin. In a second step, the specimen is counterstained with another optical enhancement factor, preferably methyl green. The resulting preparation has green nuclei with varying degrees of brown diaminobenzidine (DAB) precipitate localized in the nuclei with the estrogen receptor. While a counterstaining technique using peroxidase and methyl green is exemplary, other stains and optical enhancement factors are available which can be conjugated or attached to a particular antigen and the invention is not limited to only the example shown.

However, spectral studies have shown that the methyl green stain offers good spectral separation from the diaminobenzidine precipitate of the immunoperoxidase technique so that different features of the image can be readily separated by filtering it at two different wavelengths. This allows the image to be digitized into two separate images, one in which all the cell nuclei are optically enhanced (methyl green), and one in which only those nuclear areas with receptor staining (DAB) are optically enhanced. In a preferred embodiment, the images can be separated by a 650 nanometer (red) filter to produce an image of all of the nuclei, and a 500 nanometer (green) filter to produce an image of only those nuclear areas with the diaminobenzidine precipitate staining.

To further differentiate those areas an interactive threshold setting technique is provided where an operator visualizing the images can set a boundary on the areas under consideration. When the boundaries are set, the images are formed by eliminating all parts of the image which are below the thresholds in optical density. A threshold, termed a nuclear boundary, is set for the first image, and a threshold, termed an antibody boundary, is set for the second image.

The image processing method then consists of first forming the mask image of the nuclei under consideration with the red filter. This mask image is stored and another image for the estrogen quantitation is then acquired by using the green filtered version of the same image. The effect of the filters in combination is to optically enhance (make darker) those areas of the nuclear mask where nuclei are stained with diaminobenzidine and to make lighter those nuclei with only methyl green counterstain. An image analysis can then be performed using only those areas of the image which are stained and which are within the mask.

Another aspect of the invention provides a means for determining which area of an image field is to be measured. A window or box is displayed on the first image where the window can be moved and varied in size. This allows for the selection of particular cells to be included in the population measured and for other cells to be excluded. In this manner, the operator of the apparatus can distinguish normal cells from carcinoma cells so that a heterogeneous specimen can be measured more accurately. The feature also allows for the exclusion of debris, necrotic tissue, blood cells, etc. from the image analysis.

Statistical data of the differences between, and comparison of the two images such as a histogram may be used to quantitate the amount of estrogen receptor in the cell population under study. Also, the proportion or percentage of total nuclear area stained may be easily measured as the area stained above an antibody threshold level in the second image.

With the ability to assay not only the intensity of the estrogen receptors but also their distribution in a cell population, a method is provided by the invention for predicting favorable endocrine therapy response based upon a combination of these factors.

A cell population is measured with the apparatus of the invention to determine the percentage of positive stained cells in the population and their average stain intensity. A combination score of these two factors is made according to the formula:

$$QIC = \frac{\% \text{ of Positive stained} \times \text{Staining Intensity}}{N}$$

where
QIC = a quantitative immunocytochemical score; and
N = a scaling factor.

It has been determined empirically that when the scaling factor is 10, a QIC score of $\sim 18$ corresponds with excellent sensitivity and specificity to other quantitative and semi-quantitative estrogen receptor assays. Particularly, a QIC score of $\sim 18$ corresponds with a 98% sensitivity factor and a 100% specificity factor when compared to a biochemical assay of estrogen receptor setting an estrogen receptor rich threshold at 10 Fmol./mg. of cytosol.

For progesterone receptor assays, the methods and apparatus are the same as previously described with only specimen preparation being different. The specimen is stained using an immunoperoxidase staining technique including the use of a monoclonal antibody against progesterone.

Accordingly, it is an object of the invention to provide methods and apparatus useful in performing a quantitative image analysis for characterizing nuclear protein content, particularly steroid hormone receptors of small cytological samples and especially fine needle aspirates of breast carcinomas.

It is another object of the invention to provide an image analysis of a cell population capable of quantitating estrogen receptor or progesterone receptor of human malignancies of the breast and female genital tract.

Still another object of the invention is to provide image analysis methods useful in predicting the responsiveness of cancer patients to endocrine manipulative management.

Yet another object of the invention is to provide a quantitative measurement value of hormonal receptor which is useful in predicting estrogen or progesterone rich carcinoma samples.

These and other objects, features, and aspects of the invention will become more apparent upon reading the following detailed description when taken in conjunction with the attached drawings wherein:

DETAILED DESCRIPTION OF THE PREFERRED EMBODIMENT

Figure 1:
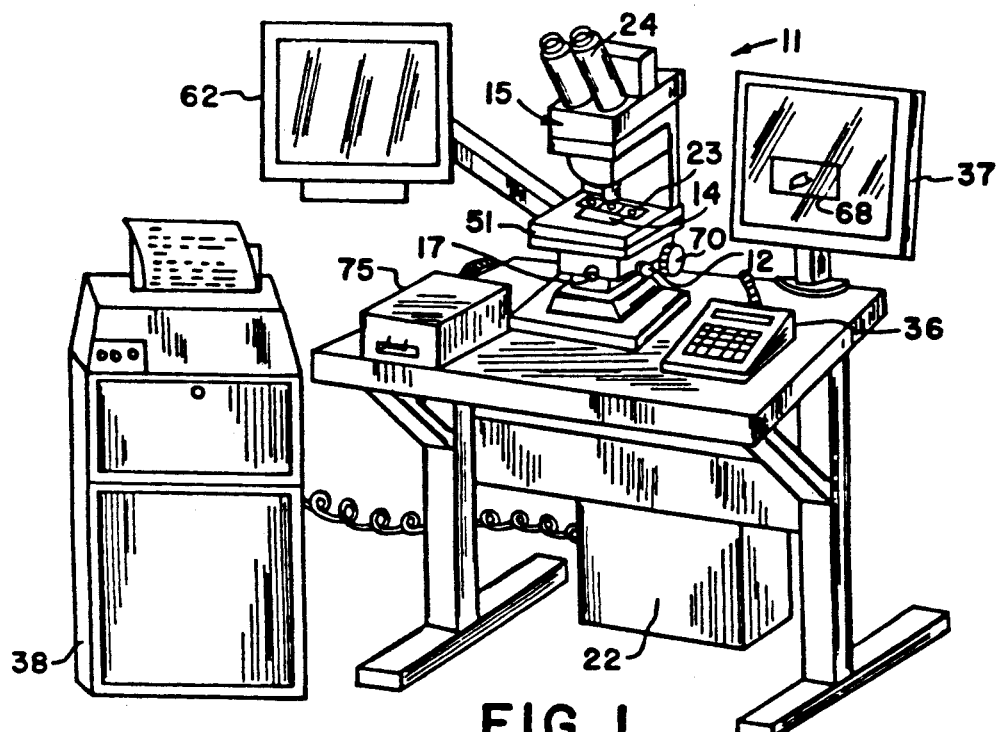
FIG. 1 is a pictorial representation of an image analysis system constructed in accordance with the invention.
Figure 2:
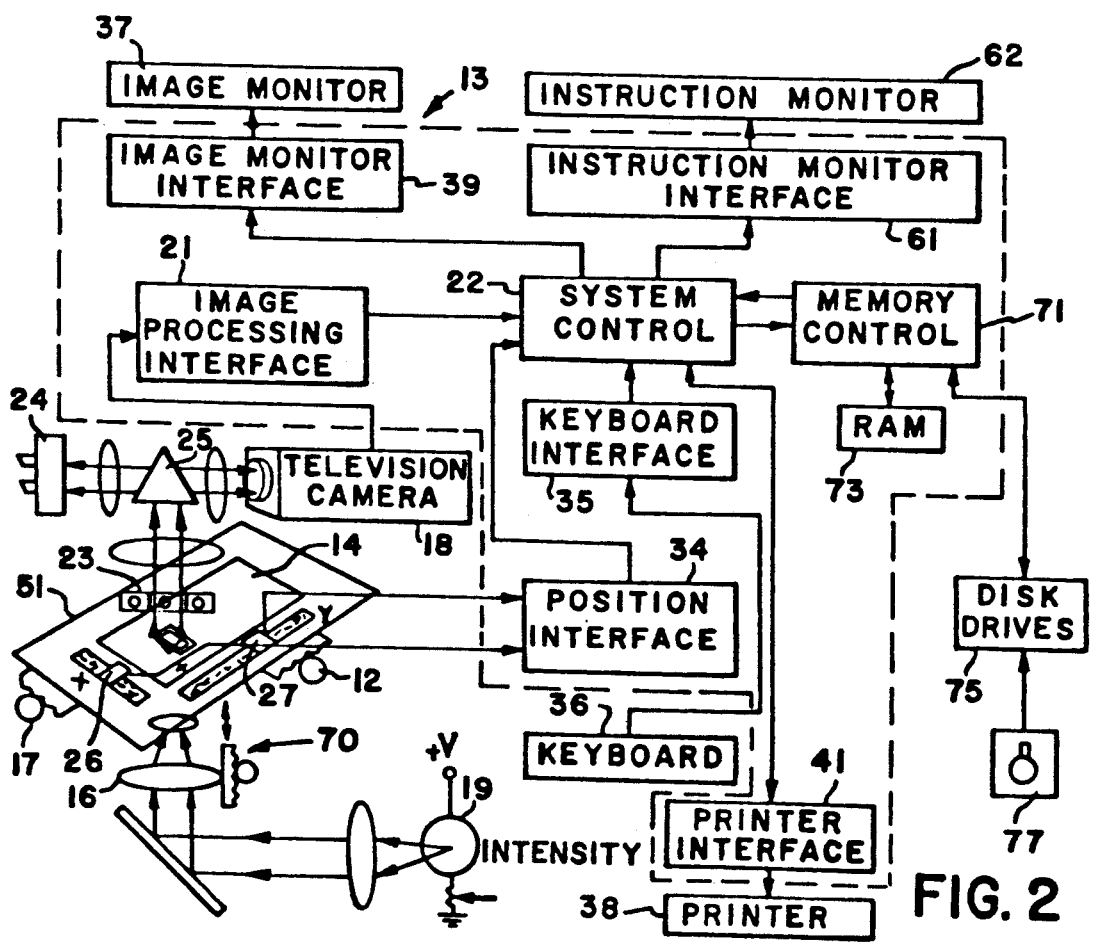
FIG. 2 is a functional block diagram of the image analysis system illustrated in FIG. 1 which is adapted to perform the methods for the quantitation of nuclear proteins in accordance with the invention.

With reference to FIGS. 1 and 2 of the drawings, the invention is embodied as an apparatus 11 (FIG. 1) which functionally operates as a digital image analysis and processing system 13 (FIG. 2). The apparatus 11 comprises a high resolution microscope 15 with which an operator can view specimens on a support, in a preferred embodiment a glass slide 14. The microscope 15 has adjustment means 70 for focusing its optics 16 on the slide 14 and a platform 51 movable incrementally in the X and Y directions by positioning means 12 and 17 in order to view different areas thereof. Positioning means 12, 17 and 70 in the form of adjustment verniers are conventional for instrument quality microscopes.

The specimens in the field under study are further viewable by the imaging system 13 via a television camera 18. The camera 18 views the light intensities of the image of the field and converts them into an analog signal which can be sampled and processed by the imaging system 13. The image analysis system 13 is controlled by a system control 22 in the form of a digital processor such as a personal computer.

An operator can interactively communicate with the system control 22 via a keyboard 36, and interacts further with the system to quantitate nuclear proteins by the viewing of two displays or monitors. A first display, image monitor 37, is a conventional RGB monitor which displays through the system control 22 and camera 18, the same image field as seen through the microscope 15. A second display, instruction monitor 62, is another conventional RGB monitor and is used to provide the operator with interactive prompts, messages, information, and instruction screens from a system program executed by the system control 22.

The keyboard 36 is preferably an AT type of function keys F1–F10, in the middle a plurality of alphanumeric keys including the special keys of ENTER, SHIFT, CONTROL, and ALTERNATE, and on the right-hand side cursor movement keys including up, down, left and right arrow keys, a numeric keypad, a number lock key, and an escape key. A keyboard interface 35 translates keystrokes into numerical codes recognized by the system control 22 for specific key indications. A printer 38 is provided for producing reliable hard copy output of the data produced by the apparatus 11.

A functional schematic of the apparatus 11 is illustrated in FIG. 2 as image analysis and processing system 13. The image processing system 13 is used to analyze a plurality of specimen cell objects on the support or glass slide 14 of the microscope 15. Suitable high resolution microscope optics 16 receive light from a variable intensity source 19 and transmit the light through the slide 14. The light is then passed through a filter selection apparatus 23 having three selectable filters. An optical image of each of the cell objects on the slide 14 passes through the filter apparatus 23 to an image splitter 25 which can take the form of a prism.

On one side of the splitter 25, the television camera 18, or other detector, converts the optical images point by point into a scanned electronic signal representing the optical intensity of each point in the image. The output of the camera 18 which is formatted as a standard NTSC analog video signal is applied to an analog to digital converter of an image processing interface 21. The image processing interface 21 samples the analog signal and converts the image signal from the television camera 18 to a digitized signal which is received and stored by the system control 22. Because of continuous scanning, a real time image of the area the optics 16 are focused on is provided by the image display 37. In general, the digital image is stored as a 512×512 array of pixels each having a measured light intensity of 0–255 (eight bits).

Because the source 19 transmits light through the cell objects on slide 14, the optical density of each pixel of the image will convert the light into a different intensity depending upon its percentage of transmission. Areas with no cell objects in them will appear relatively light or intense and areas having nontransmissive objects will appear darker. In general, unmodified cell objects are relatively transparent and their features difficult to distinguish. Staining the cell objects allows an optical enhancement of the features stained so they will appear darker than other features and their background. The invention enhances a specific nuclear protein, either estrogen or progesterone, by staining to permit its visualization by the image analysis system 13.

On the other side of the image splitter 25 are located the viewing optics 24 of the microscope 15. This parfocal arrangement allows the same image seen in the viewing optics 24 to be displayed on the image display 37. This feature allows the positioning of the platform 51 by the manual X, Y adjustment of positioning means 12 and 17 until the operator views a field of interest on the slide 14. At that time, a computer enhanced digitized image of the selected field is displayed on the image display 37 for further analysis. An X position sensor 26 and a Y position sensor 27 generate position signals to a position interface 34 which digitizes these signals to provide the apparatus 11 with an accurate coordinate representation of the field in view.

Both of the displays 37 and 62 are controlled by the system control 22 through standard video monitor interface circuitry 39 and 61, respectively. Similarly, the keyboard 36 and the printer 38 communicate with the system control 22 through conventional interface circuitry 35 and 41, respectively. In addition, the system control 22 controls a random access memory 73 and bulk memory storage in the form of either floppy and hard disk drives 75 through a memory control interface 71.

All of the interface circuits 21, 34, 35, 39, 41, 61, and 71 can be selectively embodied on printed circuit boards which are mounted in the backplane or card connector of a conventional personal computer forming the system control 22. Preferably, the personal computer can be one manufactured by the IBM Corporation having a model designation AT. Such system control 22 can be run under a disk operating system such as PC DOS, version 3.1 or later. The system software for the image analysis is called as an application program from the disk drive 75, and could, for example, be supplied on a floppy disk 77. The system software is read from disk 77 and loaded into RAM 73. After loading, program control is transferred to the analysis software to regulate the various hardware elements of apparatus 11 previously set forth in a known manner.

The image analysis system 13 operates under an interactive program control by providing a number of instruction screens or images on the instruction monitor 62 to assist the operator in the quantitation of nuclear proteins, i.e. estrogen receptors or progesterone receptors, found in one or several cell populations displayed on image monitor 37. Through interactive responses by the operator and menu selections on different instruction screens, the basic system functions of the image analysis are performed.

Figure 3:
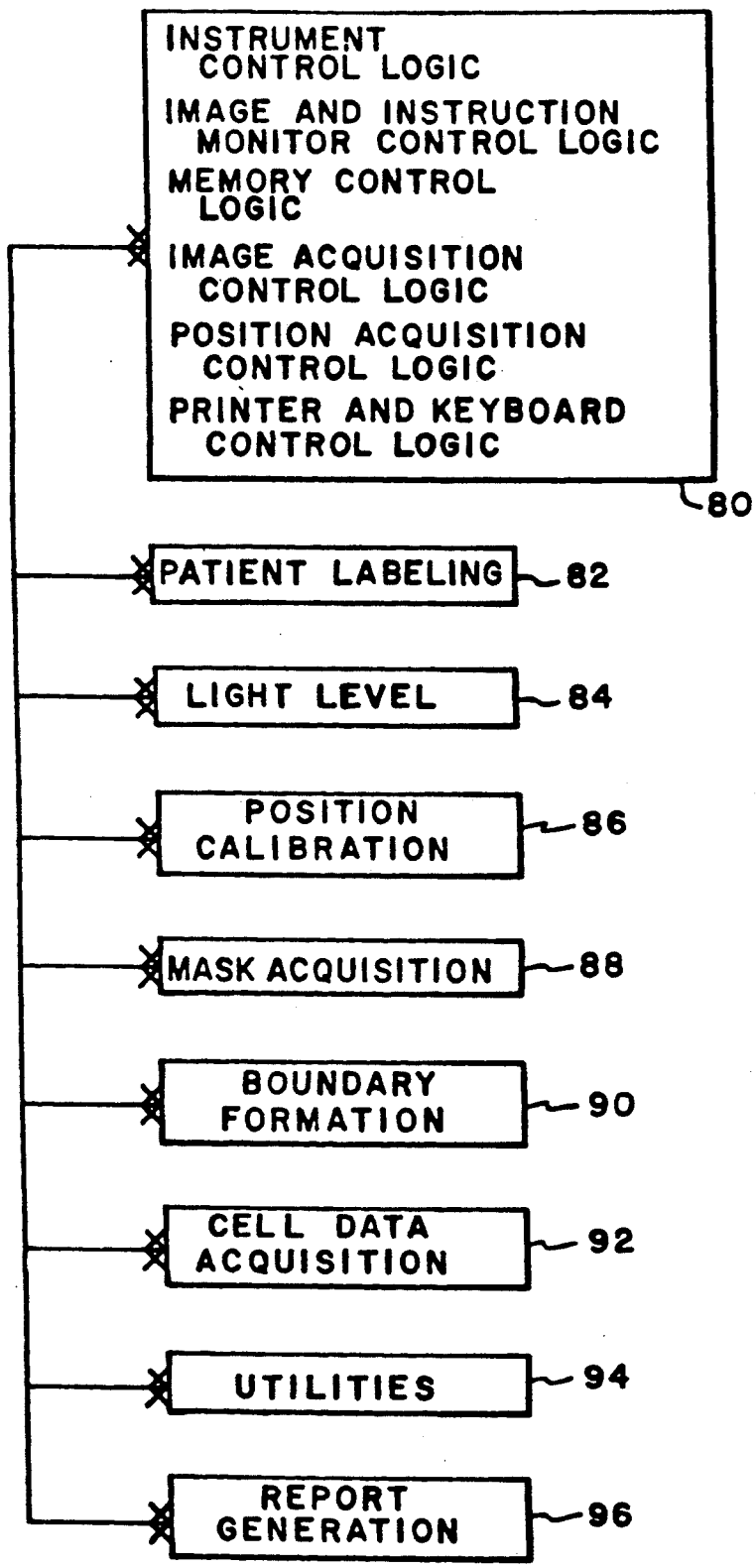
FIG. 3 is a functional system diagram illustrating the major operations of the system control illustrated in FIG. 2.

The system functions are more fully illustrated in FIG. 3 where software control logic functions for the hardware in block 80 are shown communicating with software analysis and measuring functions of the system program in blocks 82-96. Software is included in the system program to perform an initialization and an interfacing of the operating system functions and overall control of the instrument by instrument control logic. A screen handler for the instruction screens and the video display of the specimen digital images is performed for both of the monitors by image and instruction monitor control logic. The memory and disk storage are handled in the software by memory control logic. Input and output for the interactive responses and reports are handled by the printer and keyboard control logic. Further, data from the camera 18 and from the position sensors 26, 27 are handled by image acquisition control logic and position acquisition control logic, respectively.

The control logic of the software forms a operating shell which is used by the analysis and measuring functions in blocks 82-96 to control the hardware of apparatus 11 to perform the particular function needed. The system provides a patient labeling function 182 to identify the particular tissue samples which are under study. Light calibration and position calibration functions 84 and 86, respectively, are used to determine a correct reference optical density for a particular field and the location of that particular field with respect to a coordinate origin. A mask acquisition function allows a nuclear mask to be formed so as to identify the total nuclear area of an image. A boundary formation function 90 allows the operator to choose a reference level against which the grey scale values of an image are compared for a mask image or an antibody image. The cell data acquisition function 92 provides a storage of the grey scale values of a specimen image. A utilities function 94 provides the needed auxiliary type programs for assisting in the primary functions of the image analysis. A report generation function 96 is used for hardcopy production of analyzed and compiled data from the system on the printer 38.

Figure 4:
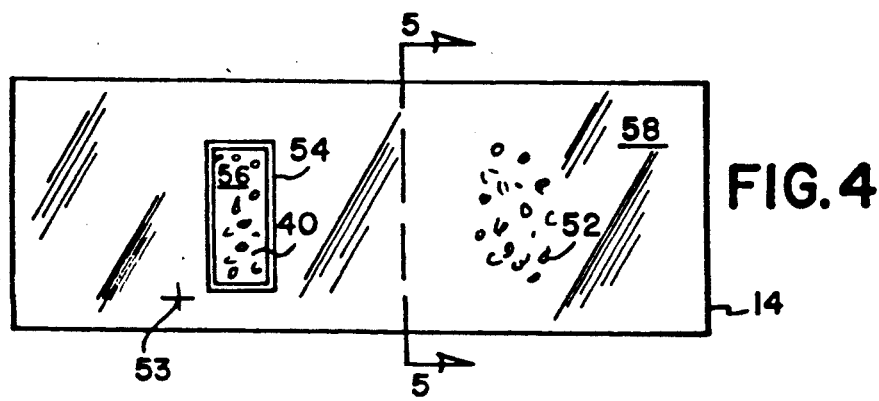
FIGS. 4 and 5 are perspective and cross-sectional views, respectively, of a slide particularly adapted for use in the image analysis system illustrated in FIG. 1 having separate areas for calibration cell objects and specimen cell objects.
Figure 5:

The support on which a specimen is viewed preferably is a transparent glass slide 14 as illustrated in FIGS. 4 and 5. Glass slides of a rectangular shape come in standardized sizes such as 1" by 3" and such can be used with the following modifications. The slide 14 is partitioned into two sections where in a first control section 56 are located control cell objects 40. In a second specimen section 58 there are located specimen cell objects 52 which are to be measured for their content of estrogen receptors. The slide 14 further includes a border 54 around the control section 56 for rapid identification purposes. Further, on some convenient location of the slide 14 is placed a identifying mark 53. The mark 53, illustrated as a cross in FIG. 4, is of a predetermined optical density and can be used as a landmark for identifying the coordinate origin for fields on the slide.

Figure 6:
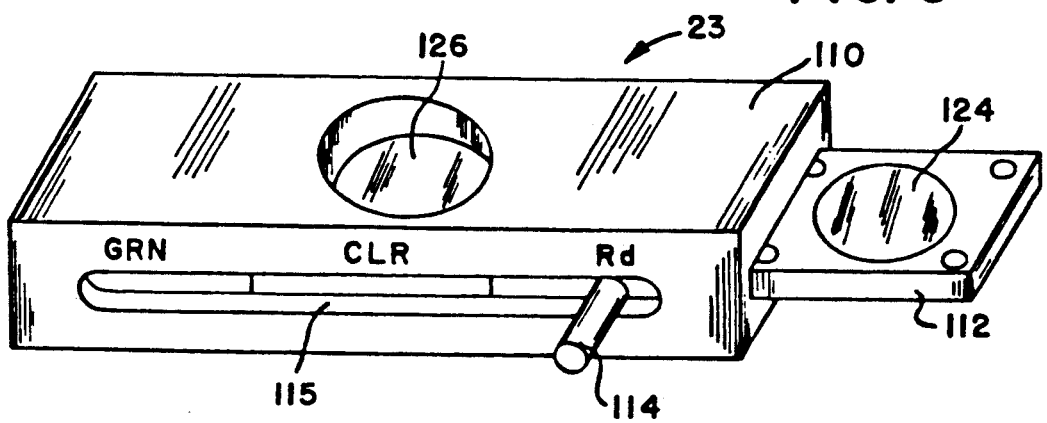
FIG. 6 is an enlarged perspective view of a one embodiment of a filter selection apparatus for the image analysis system illustrated in FIG. 1.

With respect to FIG. 6 there is illustrated a perspective view of the structure which implements the filter selection apparatus 23. The filter selection apparatus 23 includes a mounting block 110 which has a viewing aperture centrally located therein for being disposed coincidentally in the image acquisition path of the microscope 15 and analysis system 13 of the apparatus 11. A slide 112 is positionable at three positions in the mounting block 110 by means of a handle 114 guided in a slot 115. The slide 112 mounts three circularly shaped filter elements, each corresponding to one of the three positions of the handle 114. A first element 126 comprises a red filter which passes only light of a narrow bandwidth of wavelengths near $650\pm20$ nanometers. A second element centered in the slide (not shown) is a neutral density filter and does not appreciably change the optical characteristics of light passing therethrough. The third element 124 is a green filter which passes light of a narrow bandwidth of wavelengths near $500\pm20$ nanometers. Because of the narrow bandwidth of the filters 124, 126 the images passed therethrough are essentially monochromatic.

When the aperture of block 110 is positioned in the light path of the microscope 15, the operator has three choices for an image transmitted through apparatus 23 to the viewing optics 24 and the television camera 18. Positioning the handle 114 at the far right position of the slot 115 will cause a monochromatic filtering of the image with the red filter 126, positioning the handle 114 in the center location of the slot 115 will provide a substantially unfiltered image, and positioning the handle 114 at the furthest left-hand side of the slot will produce a monochromatic filtering of the image with the green filter 124.

While the illustrated filter selection apparatus 23 is shown as manually selectable, it is evident that such apparatus could just as easily have been made automatically adjustable, such as by program control. Further, the function of the filter selection apparatus 23 could be integrated in many of the other elements in the image analysis system 13 along the image path. For example, a multiple color camera could be used to replace camera 18. Additionally, prior to the image analysis, a digital or analog filtering of the electrical image signal could be accomplished. There are numerous methods by which the two monochromatic images of the microscope field can be obtained, and that shown is meant to be exemplary not limiting.

The method of quantitating nuclear proteins includes providing specimen cell objects in section 58 of slide 14 and staining them with an optical enhancement factor which specifically binds to the nuclear protein. The stain is then viewed with the image analysis system 13 to measure the optical density of the stain for intensity measurement and to locate the areas in which stain is found for distribution measurement. Because the intensity of the staining relates to the quantity of the nuclear proteins, measurement of the different optical densities of the stain permits a direct measurement of the quantity of the proteins. As an enhancement, control cell objects can be placed in section 56 of slide 14 to provide a normalization or reference optical density for the staining. Further, one or several counterstains can be used to further distinguish among several features of the cell objects.

Figure 7:
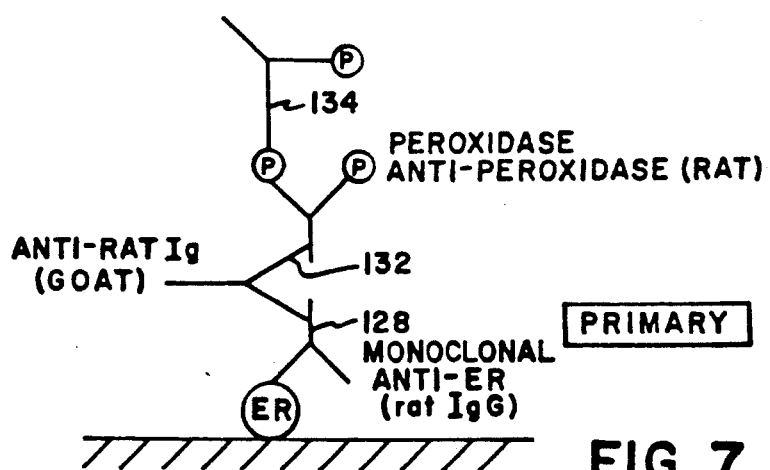
FIG. 7 is a pictorial view at the microscopic level of the binding effects of a monoclonal antibody against estrogen receptor sites, a bridging antibody, and a peroxidase-antiperoxidase complex.
Figure 8:
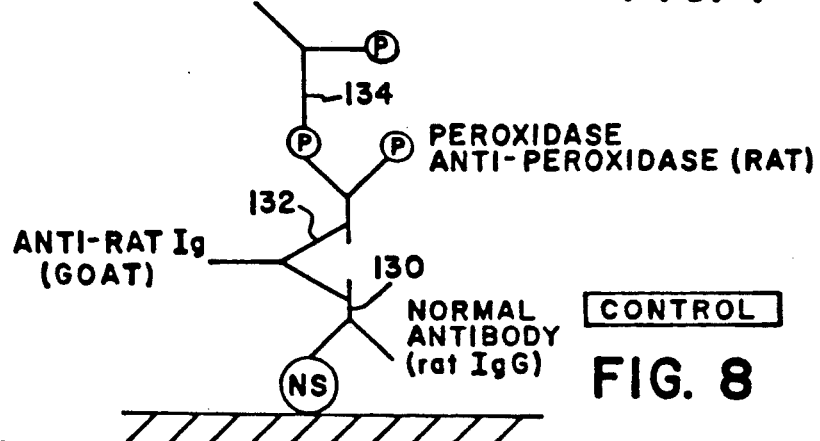
FIG. 8 is a pictorial view at the microscopic level of the binding effects of a control monoclonal antibody (immunoglobulin) against nonspecific receptor sites.

Preferably, in one particular embodiment, the staining method employs a sensitive peroxidase-antiperoxidase technique for visualization of estrogen or progesterone receptors in specimens through the use of monoclonal antibodies directed specifically against those receptors. A diagrammatic representation of the process on the microscopic level is illustrated in FIGS. 7 and 8. Two portions of a human tumor specimen containing a cell population from which the estrogen receptors are to be measured are placed on the two separate sections of the slide 14 and suitably fixed thereto as by tissue adhesive. The separate sections are then fixed in separate washes of formalin, methanol, and acetone, and, thereafter, treated with a blocking reagent to prevent nonspecific binding of the subsequent reagents.

The part of the specimen cells to be measured is incubated with a primary antibody, a monoclonal antibody (rat) to human estrogen receptor in the specimen portion 58 of slide 14. This antibody, as represented at 128, binds specifically to the estrogen receptor sites ER of this tissue portion. The other portion of the specimen in the control section 56 of the slide 14 is incubated with a control, normal rat IgG, represented at 130. The purpose of the control 130 is to evaluate the amount of binding of the immunoperoxidase reagents in this technique to nonspecific sites NS of the specimen to yield a background measurement.

Both sections 56 and 58 of the slide 14 are then incubated with a bridging antibody, an anti-rat immunoglobulin (goat) illustrated at 132 in both figures. The bridging antibody 132 binds to the rat antibody 128 against human estrogen receptor in the specimen section 58 and to any bound normal rat IgG 130 in the control section 56.

A rat PAP complex 134 is added to both sections 56 and 58 of the specimen and binds to the anti-rat Ig bridging antibody at 132. After this step, a solution containing hydrogen peroxide and diaminobenzidine.4HCl (DAB) is added to the specimen and control sections. The reaction of the peroxidase with hydrogen peroxide converts the bound DAB present into an insoluble reddish brown precipitate. The proportion of the precipitate and its location are influenced by the binding positions of the PAP complex and, through the bridging and primary antibodies, the locations and amounts of the estrogen receptors in the specimen.

The concentrations, timing, and chemical compositions of the reagents used in this staining method are more fully described in the previously referenced paper by McCarty Jr. et al. Preferably, the monoclonal antibody which is used to bind to the estrogen receptor sites is one of those developed at the University of Chicago and designated H222 sP2 and H226 sP2, and that which is used to bind to the progesterone receptor is one which is commercially available from Transbio Sarl 6 Rue Thiers, Paris France and designated mPRI.

It is further evident that instead of a single slide, as shown for the preferred embodiment, separate slides can be used in the staining technique for the control portion and the specimen portion. Whether a single slide or two separate slides are used does not alter the quality or amount of staining of the immunoperoxidase stain which binds to the receptors of a specimen.

The DAB precipitate is then visualized by image analysis with apparatus 11 to determine the quantitation of the estrogen receptors in the specimen. In general, the brown precipitate does not transmit light well and will show up as dark areas in the cells of the specimen. The optical density and hence pixel intensity will be related directly to the amount of DAB precipitated and to the quantity of estrogen receptor which has bound the antibodies. To be able to more clearly visualize the nuclear area of each cell, a counterstain of methyl green is added. It is important to note that both the primary stain of DAB precipitate and the counterstain of methyl green are specific to the nucleus of each cell. This means that debris and other cellular features will appear lighter in the microscope image and can be distinguished.

A dual filtering method is thereafter applied to distinguish the areas stained by the DAB and the areas stained by the methyl green. The red and green filters 126 and 124 respectively are used by moving handle 114 to form monochromatic images of the cell objects which can be stored in the apparatus 11. These images, one by the red filter and the other by the green filter, are used to separate the primary stained areas from the nuclear areas, and to separate the nuclear areas from other cell or field features.

Figure 9:
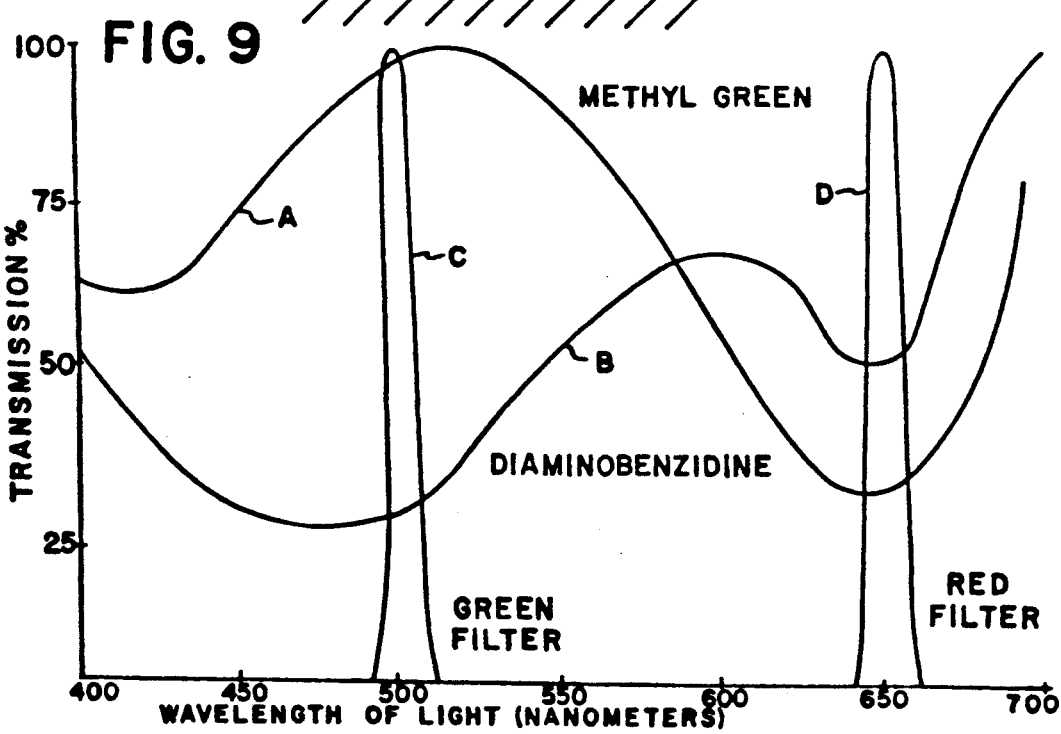
FIG. 9 is a graphical representation of the % of light transmission as a function of light wavelength for the two counterstains and the two color filters used in accordance with the invention.

The results and desirability of this dual filtering of a counterstained cell image are more fully illustrated in FIG. 9. The percentage of light transmitted through the nuclei stained with methyl green is shown in the curve A as a function of the wavelength of light. The percentage of transmission of light for diaminobenzidine (DAB) is shown in curve B as a function of the wavelength of light. The bandwidth of wavelengths of light passed by the green filter is illustrated in band C while the bandwidth of wavelengths of light passed by the red filter is illustrated in band D.

When an image of a counterstained cell population or specimen is filtered with the green filter 124, substantially all of the areas stained with the methyl green will be invisible. This is because the methyl green curve A has a relative transmissive peak near this wavelength band while the diaminobenzidine curve B is relatively nontransmissive in this band. Thus, the areas with primary DAB stain can be separated from the nuclear areas. At the other extreme of the graph, the band D of the red filter is positioned at a place where just the opposite occurs. The methyl green curve A has a relatively nontransmissive valley in this bandwidth while the diaminobenzidine curve B is also relatively nontransmissive. Thus, the nuclear areas containing both the primary stain and the counterstain appear darker than other cell features and can be identified without a problem.

Because of the relative differences in light transmission between the primary and counterstain in the two filtered bandwidths, the methyl green stained area is enhanced during one filtering relative to other areas of the cell, and the areas which have diaminobenzidine precipitate are enhanced relative to the methyl green areas during the other filtering. Thus, the nuclear areas of the cell objects are optically enhanced along with the areas having DAB precipitate.

While the implementation shows a convenient and advantageous method for discriminating between the two areas having counterstaining, it is recognized that there are various other staining or optical enhancement methods and filtering methods which can be used to optically enhance one particular area or feature over another cell feature. For the quantitation of the specific hormonal receptors shown (progesterone and estrogen receptors), what is important is to distinguish the nuclear area in total so that it can be compared to that nuclear area which contains receptors by the presence of the diaminobenzidine precipitate.

Figure 10:
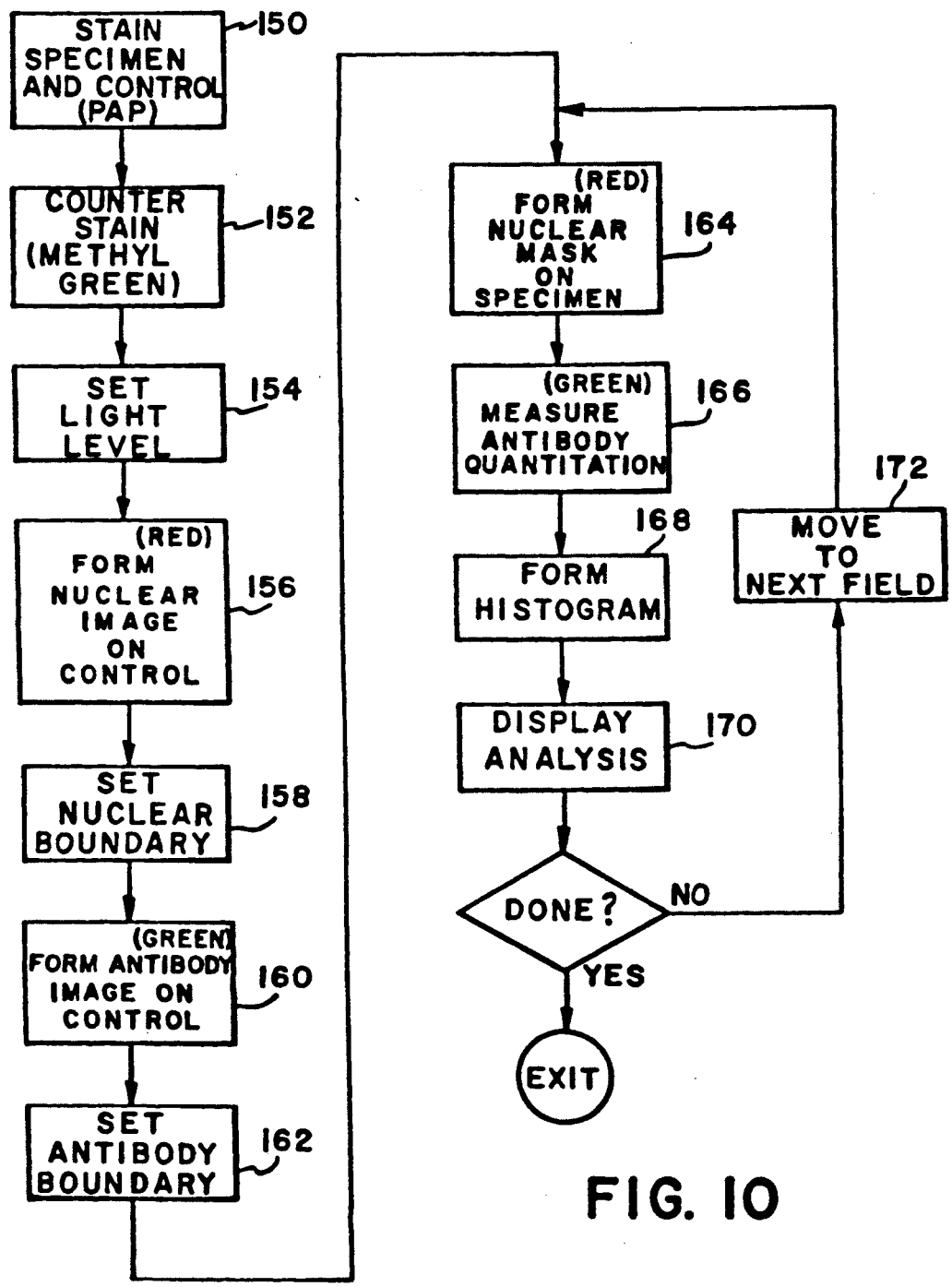
FIG. 10 is a functional flow chart of one preferred method of quantitating hormonal receptor for human carcinoma in accordance with the invention.

A functional flow chart of the method of analyzing and quantitating hormonal receptors with the dual filtering technique is shown in FIG. 10. In a first step, block 150, the specimen and control sections 56, 58 of a slide 14 are stained as described previously with the immunoperoxidase staining technique using the monoclonal antibody against estrophilin, or the one against progesterone, for the specimen section, and a control antibody for the control section. The specimen and control sections 56, 58 then contain similar cell populations but with different amounts of primary stain. The specimen and control sections 56, 58 are thereafter counterstained with a methyl green stain in block 152.

Figure 11:
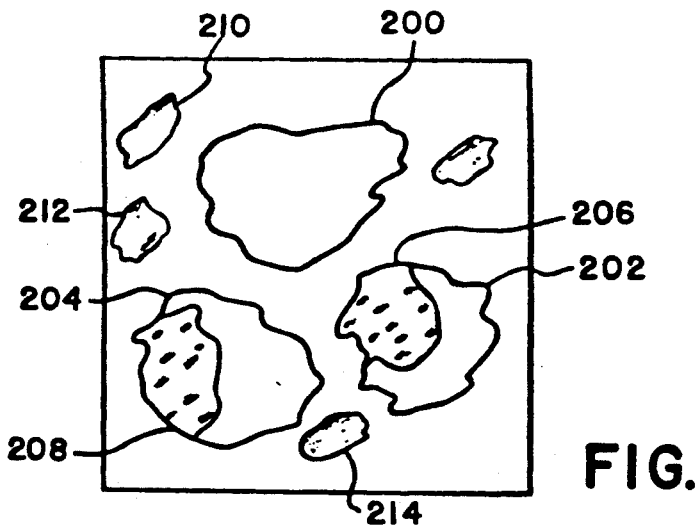
FIGS. 11, 12, and 13 are pictorial representations of images of a cell population showing an unfiltered image, a red filtered image, and a green filtered image, respectively.

The resulting preparation has green nuclei with varying degrees of brown diaminobenzidine precipitate. An unfiltered representation of a small section of a cell population image is shown in FIG. 11 where 200, 202, and 204 are green cell nuclei and where nuclei 202, and 204 have brown areas 206, and 208, respectively of DAB precipitate. Nucleus 200 does not contain any estrogen receptor and therefore does not have any DAB precipitate. Objects 210, 212, and 214 are various other cell features or debris from the tissue section.

A calibration procedure is done in blocks 154-162 in order to establish three variables for the dual staining technique. The first variable is the light level which is set in block 154. The calibration is done on the control section 56 or, as mentioned previously, on a separate control slide. Because grey scale images of optical density are analyzed, the level of the background light is important as these values are representative of the % transmission of a reference level of light. Therefore, when calibrating the light level, the variable source 19 is adjusted at a clear portion of slide 14 until the instrument recognizes it is set at the correct reference level.

The control cell section is then imaged with the red filter in block 156 so that background and other features of the cells can be eliminated from the image and nuclear areas will stand out. The cell nuclear boundaries however must be distinguished to accurately display the areas, and this necessitates the formation of a reference grey level or nuclear boundary threshold.

A threshold is set for the recognition of positive grey levels for the nuclei in block 158. Positive nuclear grey levels are pixel levels above which a nucleus boundary will be recognized from background. Due to different amounts of methyl green staining, to different reactions of the immunoperoxidase staining on different specimens, and to the different quantity of nonspecific binding, the grey level representing the nuclear boundaries of the specimen cells will vary. By identifying a nuclear boundary reference level for the control cells, which come from the same specimen and are counterstained identically to the specimen cells, a threshold for the measurement of any number of different fields in the specimen cells can be set.

After the nuclear boundary level has been stored, the apparatus 11 is used to make an image of the same field of control cells using the green filter in block 160. As was the case for the nuclear area, the boundaries of the DAB stained areas must be set by forming a threshold or antibody boundary level.

A threshold is set for the recognition of positive grey levels for the antibody stains in block 162. Positive antibody grey levels are pixel levels above which the ER stain will be recognized from background. Thus, this threshold level is set to just above the highest grey level of the control cell nuclei. This threshold is necessary to determine the contribution of the nonspecific staining of the control cells and the contribution of the counterstain, methyl green, to the total stain detected by the instrument. This antibody reference level permits the discrimination between antibody negative stained cells and antibody positive stained cells. After its determination, the antibody boundary level is stored in memory 73.

Figure 12:
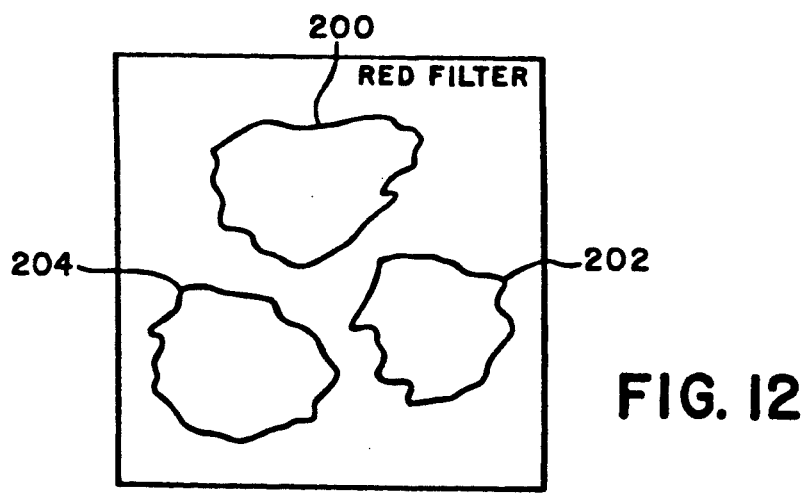

After the image analysis system 13 is calibrated and the tissue sample is labeled, a nuclear mask image is formed of the specimen cells in the field of interest using the red filter in block 164. The threshold set in the calibration operation is used for this function. The nuclei because of the counterstaining and filtering stand out in the image as seen in FIG. 12 while the DAB areas are not visible. This filtered image is stored as the nuclear mask image and is representative of the total nuclear area of the particular field. The red filter is then changed to the green filter and an antibody quantitation image is formed in block 166 from the same specimen field. The filtered image, using the antibody boundary level of the calibration step, has the brown DAB precipitate areas which stand out prominently from the rest of the cell features.

Figure 13:
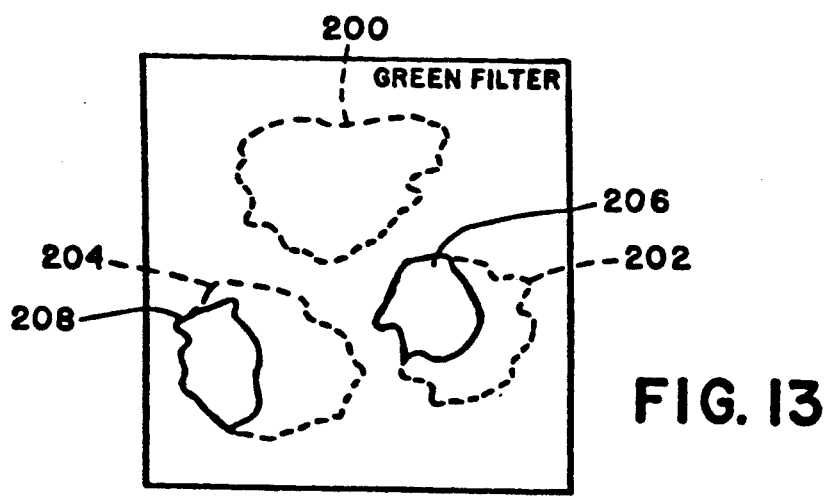

Thereafter, the nuclear mask image can be used to overlay the antibody image after it is filtered with the green filter. A representation of this combination is shown as FIG. 13 which illustrates that only those areas having precipitate 206, and 208 and which are within the nuclear areas are recorded.

A number of important parameters relating to the content of estrogen receptor in the nuclei are then available by this technique. A measurement of the optical density of the areas 206 and 208 with instrument 11 will give a direct indication of the quantity of estrogen receptor. The intensity values from the image can be displayed in a histogram in block 168. Further, a comparison of the nuclear area of the estrogen receptors, area 206 added to area 208, when compared as a percentage of total nuclear area, areas 200, 202 and 204 added together, will yield an indication of the distribution of estrogen receptor. Still further, by combining the quantity measurement of estrogen receptor with the distribution measurement, an indication of the prognosis of endocrine therapy can be obtained.

Such parameters are available as an analysis display in block 170. After performing measurement and analysis for one field, the operator of the apparatus 11 can stop the process, or can continue to measure more fields by moving the microscope 15 to the next field with adjustment means 12, and 17 and starting over with block 164.

The same calibration values which were found in blocks 158, 162 are used for the boundaries of each field.

While one particular pairing of a chromagen and counterstain have been preferably indicated, it is evident that many others could be used to specify a particular nuclear protein and amplify it for visualization, and pairing such with another counterstain for nuclear visualization would also be evident. The following table indicates other preferred chromagens and counterstains useful in the quantitation of nuclear proteins by image analysis. The list is not exhaustive and is suggestive of other equivalents for nuclear protein quantitation involving dyes with single immunoenzyme tagged monoclonal antibodies and counterstain, or paired immunoenzyme monoclonals utilizing different dyes.

EQUIVALENT CHROMOGENS AND NUCLEAR COUNTERSTAINS FOR QUANTITATIVE IMAGE ANALYSIS

| Enzyme | Chromogen | Counterstain |
|---|---|---|
| horseradish peroxidase | DAB (brown) 4-Cl-1-naphthol (grayish blue)[1] alpha-naphthol followed by pyronin[2] (reddish pink) 2,2'-oxydiethanol-4-chloronaphthol (black)[3] | methyl green hematoxylin nuclear fast red toluidine blue |

[1] Reaction products are soluble with organic solvents. Do not use alcohol to dehydrate tissue sections. A water soluble medium, e.g. chrome glycerin jelly, must be used to mount the cover slips. Method in Farr and Nakane: J. Immunol. Meth 47: 129–144, 1981.
[2] Reaction product is soluble with organic solvents. Method in Taylor CR, Burns J: J. Clin. Pathol. 27: 14–20, 1974.
[3] Method in Van Rooijen N, Streefkerk JG: J. Immunol. Meth. 10: 370–383, 1976.

With the ability to assay not only the intensity of the estrogen receptors but also their distribution in a cell population, a method is provided by the invention for predicting favorable endocrine therapy response based upon a combination of these factors. A cell population is measured with the apparatus of the invention to determine the percentage of positive stained cells in the population and their average stain intensity. A combination score of these two factors is made according to the formula:

$$QIC = \frac{\% \text{ of Positive stained} \times \text{Staining Intensity}}{N}$$

where
QIC = a quantitative immunocytochemical score; and
N = a scaling factor.

It has been determined empirically that when the scaling factor is 10, a QIC score of $\geq 18$ corresponds with excellent sensitivity and specificity to other quantitative and semi-quantitative estrogen receptor assays. Particularly, a QIC score of $\geq 18$ corresponds with a 98% sensitivity factor and a 100% specificity factor when compared to a biochemical assay of estrogen receptor setting an estrogen receptor rich threshold at 10 Fmol./mg. of cytosol.

EXAMPLE

Two hundred cases of primary breast carcinoma accessioned from the Duke University Endocrine Oncology Laboratory were used in a study to compare the methods of the invention and apparatus 11 to two known estrogen receptor tests, the biochemical assay and the subjective visual scoring by immunohistochemistry. These cases represented primary breast cancer specimens with sufficient cancerous tissue for complete biochemical and immunocytochemical analysis.

For each case, a biochemical estrogen receptor analysis was performed at the time the tissue was first obtained. These consisted of multiconcentration titration analysis (dextran coated-charcoal analysis) and/or sucrose density gradient analysis of estrogen binding.

For immunocytochemical analysis cryostat sections of fresh frozen tissue were fixed on slides in 3.7% formaldehyde-0.1M phosphate buffered saline for 10 minutes followed by immersion in 100% methanol for 4 minutes and acetone for 1 minute. Monoclonal antibody H222 sP2, prepared against human estrogen receptor protein was used.

The peroxidase anti-peroxidase method for immunocytochemical localization was performed as described by Sternberger. The blocking reagent was normal goat serum. The primary antibody (H222 sP2) which is a rat monoclonal antibody against human estrogen receptor, was used at a minimum concentration of $0.1 \leq g/ml$. The bridging antibody was goat anti-rat immunoglobulin and the PAP complex was of rat origin. Control slides consisted of an adjacent tumor section to that stained with the primary monoclonal antibody in which the monoclonal antibody was replaced by normal rat immunoglobulin. The peroxidase localization was developed with diaminobenzidine-$H_2O_2$. The slides were rinsed in running tap water for 5 minutes and then dehydrated in serial alcohols to xylene, and coverslipped with Permount without counterstaining.

Computerized image analysis for one immunocytochemical assay was done using the apparatus illustrated in FIG. 1. Each case consisted of three slides: a hematoxylin and eosin stained slide, a control slide and the primary H222 sP2 stained slide. The control and primary slide were counterstained with methyl green for this part of the study to aid in the visualization of the cellular morphology. The coverslips were removed by soaking the slides in toluene. They were then placed in sodium acetate buffer, rehydrated through an acetone series, counterstained with methyl green, rinsed with sodium acetate buffer, dehydrated with an acetone series to xylene and coverslipped with Permount.

The control slide was examined at 10× for an overall view of the tumor and counterstained intensity, and an area that was representative of the tumor with no tissue folding and minimal background staining chosen. The control antibody threshold was then determined at 40×. The primary section for estrogen receptor was then evaluated. An overall screen for tumor and stain was accounted for at 10×. Five random fields at 40× were then evaluated for chromagen-diaminobenzidine (DAB) intensity. If the staining intensity was focally positive and negative, and heterogeneous staining existed elsewhere in the section, a field representing the positive and negative site as well as the heterogeneous area was obtained and averaged.

In calculating the nuclear threshold the value taken was that in which the tumor cells were best represented by a pixelled image on the image monitor 37 with the control slide. If a pixelled image of the tumor cells on the primary slide was not complete, the threshold was brought up or down accordingly. This was true for all 5 fields.

The antibody threshold was determined on the control slide by viewing the image monitor 37 and increasing or decreasing the threshold until no pixelling was present and then brought up one step to account for the background staining on the primary slide. The primary slide was then observed and, if the histogram did not clearly separate the positive and negative cells, the first field was adjusted accordingly. It was never adjusted more than 3 units above or below the original control slide antibody threshold value. This was done only for the first field. The fields were averaged to give the final calculations (percent positive, percent staining intensity and QIC score), and a histogram.

Biochemical assays were summarized as fmol of estrogen binding per mg of cytosol protein.

The visual immunocytochemical localization was scored in a semi-quantitative fashion incorporating both the intensity and the distribution of specific staining. The evaluations were recorded as percentages of positively stained target cells in each of 4 intensity categories which were denoted as 0 (no staining), 1+ (weak but detectable above control), 2+ (distinct), and 3+ (intense). For each tissue, a value designated the HSCORE was derived by summing the percentages of cells stained at each intensity multiplied by the weighted intensity of staining:

$$HSCORE = Pi(i+1)$$

where i=1,2,3 and Pi varies from 0 to 100%. An HSCORE was assigned with and without methyl green counterstain.

Computerized image analysis was complete on all of the cases and a QIC score was then generated using the formula above.

The comparison of the results of each type of test showed that the computer image analysis shows excellent correlation to the two other recognized tests. In particular, of the 200 initial cases, 100 were used for comparison against results of the other two tests as shown in the table below.

|  | OIC ≥ 18 | | OIC < 18 | |
| --- | --- | --- | --- | --- |
|  | TP | FP | TN | FN |
| VISUAL SCORING | 74 | 1 | 24 | 1 |
| BIOCHEMICAL ANALYSIS | 75 | 0 | 24 | 1 | where
TP = true positive
FP = false positive
TN = true negative
FN = false negative
Image analysis for sensitivity against visual scoring is TP/TP + FN = 74/75 = 98%
Image analysis for specificity against visual scoring is TN/TN + FP = 24/25 = 96%
Image analysis for sensitivity against biochemical analysis is TP/TP + FN = 75/76 = 98%
Image analysis for specificity against biochemical analysis is TN/TN + FP = 24/24 = 100%

Figure 16:
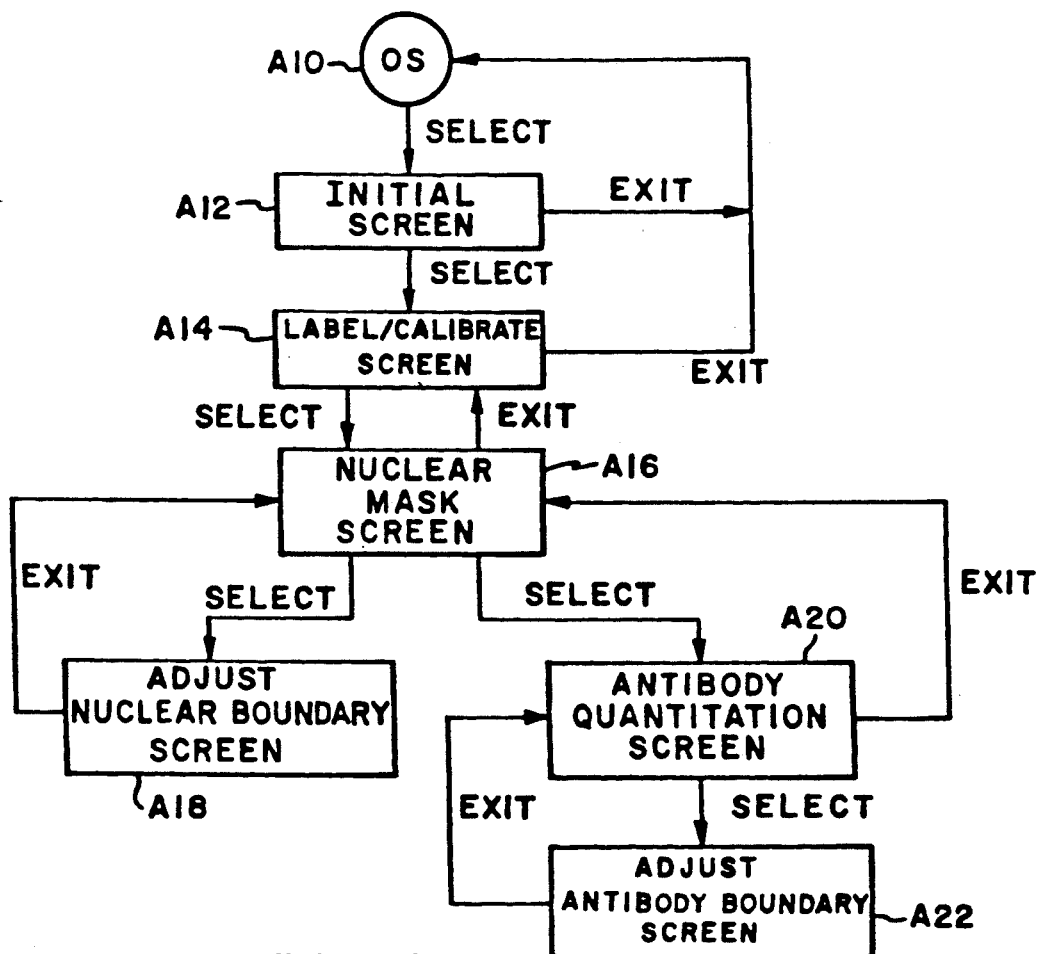
FIG. 16 is a system flowchart of the analysis screen architecture of the image analysis system illustrated in FIG. 1.

The system program in general is a menu driven program which allows the operator to interactively communicate with the image analysis system 13 to produce the quantitation of nuclear protein by image analysis. The system program displays a plurality of images or instruction screens on the instruction monitor 62 which include menus from which to select the various functions needed for performing a quantitative nuclear protein assay. FIG. 16 illustrates the screen architecture of the system and the paths that the system takes between screens. Examples of two of the system screens, the nuclear mask screen A16 and the antibody quantitation screen A20, which appear on the instruction monitor 62 are pictorially illustrated in FIGS. 14, and 15, respectively.

Returning to references in FIG. 16, the system program may be run by calling it as an application program of the operating system A10. Selection of the system program by the operating system A10 produces the initial screen A12 on the monitor 62. From the initial screen A12 the operator can select a label/calibrate screen A14 or exit back to the operating system. The operator may also exit back to the operating system from the label/calibrate screen A14. While displaying the label/calibrate screen A14 the instrument can be calibrated to provide the background or reference light settings which will be used in the measurement of the assay. Once the light calibration is complete the operator can select the nuclear mask screen A16 which is used to form a nuclear mask which will be later used in the assay technique.

One of the options in the nuclear mask screen A16 is to adjust the nuclear boundary which assists in forming the mask. Once the nuclear mask has been produced by the nuclear mask screen A16, the operator can select the antibody quantitation screen A20 to actually do measurements and generate reports. One of the options in the antibody quantitation screen is to select the adjust antibody boundary screen A22 which assists in the assay technique. Exits from the adjust antibody boundary screen A22 are to the antibody quantitation screen A20 which exits back to the nuclear mask screen A16.

In this manner an advantageous screen architecture is formed which can be easily used and understood by the operator. This screen structure facilitates the interactive measurement of the particular nuclear protein under study. The instruction screens provide an interactive use of the digital imaging system which combines the power of the system software and hardware with the judgment and knowledge of the operator. The screen structure automates the assay task of nuclear protein quantitation while still permitting the operator to selectively choose the input data and control the process to a considerable degree.

Each screen A12-A22 contains a menu of the functions permitted for use while that particular screen is being displayed on the instruction monitor 62. The function that the system is to currently execute is chosen by the operator with a cursor movement method using the standard cursor control keys of keyboard 36. While a particular screen is being shown on the monitor, the cursor movement keys are operable to position the cursor next to a particular function of the menu on that screen. While the cursor highlights the function by its position, the operator may select the function for execution by pressing the enter key.

Figure 17:
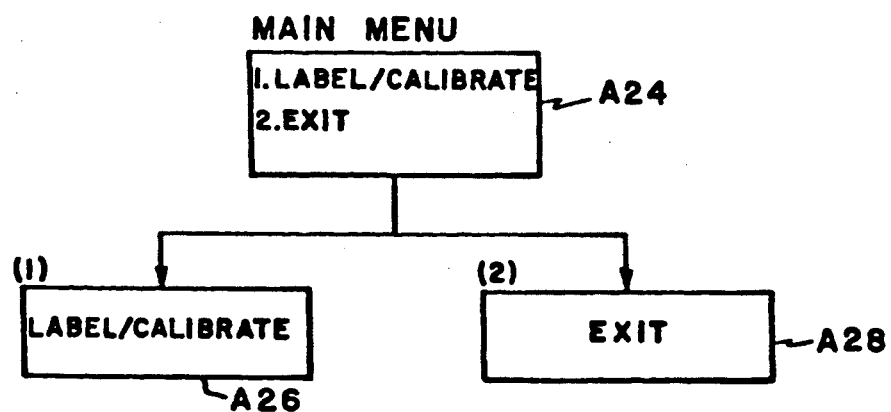
FIG. 17 is a functional flow chart of the main menu of the initial screen illustrated in FIG. 12.

The initial screen A12 contains the main menu for the nuclear protein quantitation program. The main menu illustrated in FIG. 17 has two choices which are to select either 1) a label/calibrate function, or 2) an exit function. Selection of the exit function will return control to the operating system A10 so that the processor may execute other application programs or be used as a general purpose computer. The selection of the label/calibrate function will cause the program to change the display on instruction monitor 62 from the initial screen A12 to the label/calibration screen A14. The label/calibrate screen contains a number of functions which will allow the operator to calibrate the level of background light from source 19, type in patient information, set the xy coordinates for the present field, and to access the nuclear mask screen A16. An exit function will cause the exit of the system program back to the operating system.

Figure 18:
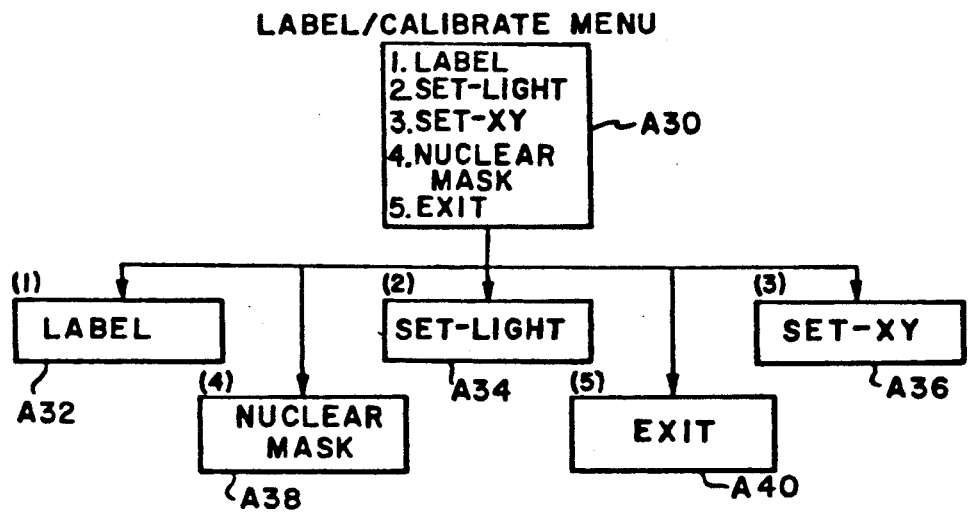
FIG. 18 is a functional flow chart of the label/calibrate menu of the label/calibrate screen illustrated in FIG. 12.

The selections of the label/calibrate menu are shown in FIG. 18 and include the choices of 1) label, 2) set-light, 3) set-xy, 4) nuclear mask, or 5) exit. The label function A32 allows the operator to enter information regarding patient identification and accession number by an interactive editing routine. Because this information is general to the estrogen receptor assay, it will appear on every screen A14–A22. The operator presses the enter or the escape key to exit the label operation. Pressing the enter key will save to memory 73 any changes which were made to the information during the function, and pressing the escape key will cause the system to ignore any changes which were made. The information which is input during the label function A32 will not be saved when the system program is exited to the operating system.

The set-light function A34 calculates the average light level (grey scale value) for the current image and allows the operator to interactively adjust the level by variation of the intensity of source 19 until it is at a correct reference level. The operator views the field of the slide 14 on the image month 37 and positions the slide with adjustment means 12 and 17 (FIG. 1) until a clear field is found. The set-light function A34 must be successfully performed at least once to be able to select the nuclear mask function. The set-light function A34 is successful when the current image is blank and the light level is set between 129 and 131, preferably 130 for the most accurate results. The image acquisition control logic will perform noise subtraction, if the set-light function A34 has been successfully executed.

The set-xy function A36 is utilized by the operator to set the current image location as the origin of an xy coordinate system for the slide. Thus, the set-xy function A36 should be used every time a new slide 14 is selected. If the set-xy function is not executed then the xy function A56 (FIG. 19) in the program will not be able to be selected by the operator. Further, if the microscope platform 51 is being moved when the set-xy function A36 is in progress, then the function may not be successfully performed. A message will appear on the screen A14 to let the operator know if the set-xy function has been successfully executed. Upon a non-successful execution of the set-xy function, the operator has to reselect the function.

Figures 14, 15:
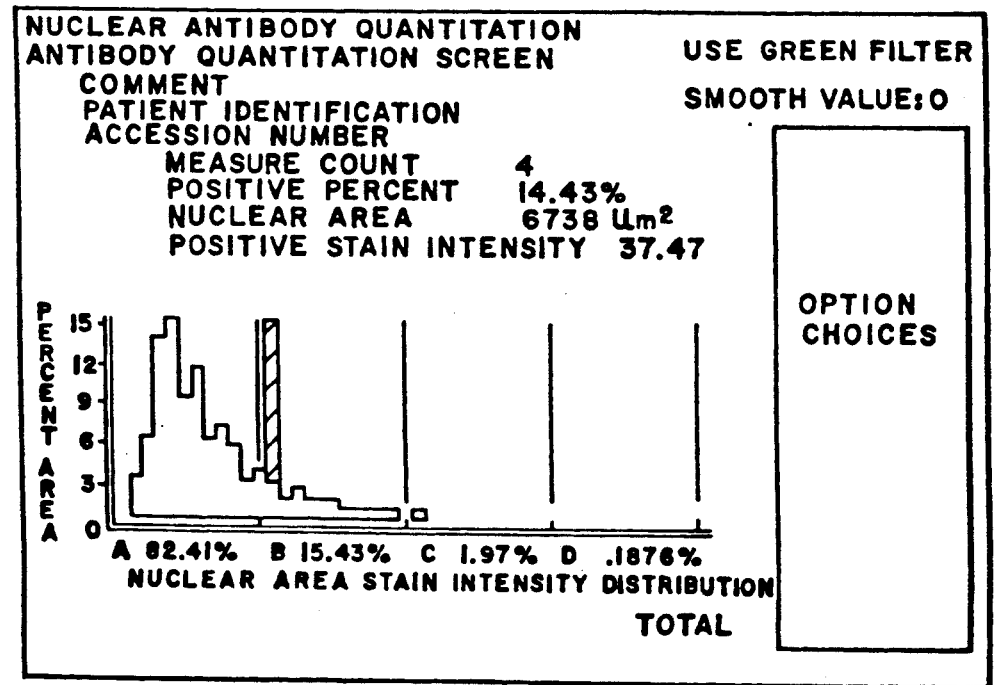
FIG. 14 is a pictorial representation of the nuclear mask screen which appears on the instruction monitor illustrated in FIG. 1.
FIG. 15 is a pictorial representation of the antibody quantitation screen which appears on the instruction monitor illustrated in FIG. 1.

Selection of the nuclear mask function A38 will change the display on the instruction monitor 62 from the label/calibrate screen A14 to the nuclear mask screen A16 which is shown in FIG. 14. The nuclear mask screen A16 contains a menu having selections which allows the operator to adjust the nuclear boundary, display the nuclear area, specify an area of an image to analyze, display the current light level, display the xy coordinates of the present field, access the antibody quantitation screen, cr clear the data from the storage. The only requirement before using the nuclear mask function is that the set light function A34 of FIG. 18 must have been successfully executed previously.

The exit function of this part of the program allows the operator to exit the system program by either selecting the escape key or the exit function. When the exit operation is specified, the user will be asked to confirm his decision to exit. To accept the confirmation the operator selects the yes key and to reject the confirmation, the operator selects the no key or presses the escape key.

Figure 19:
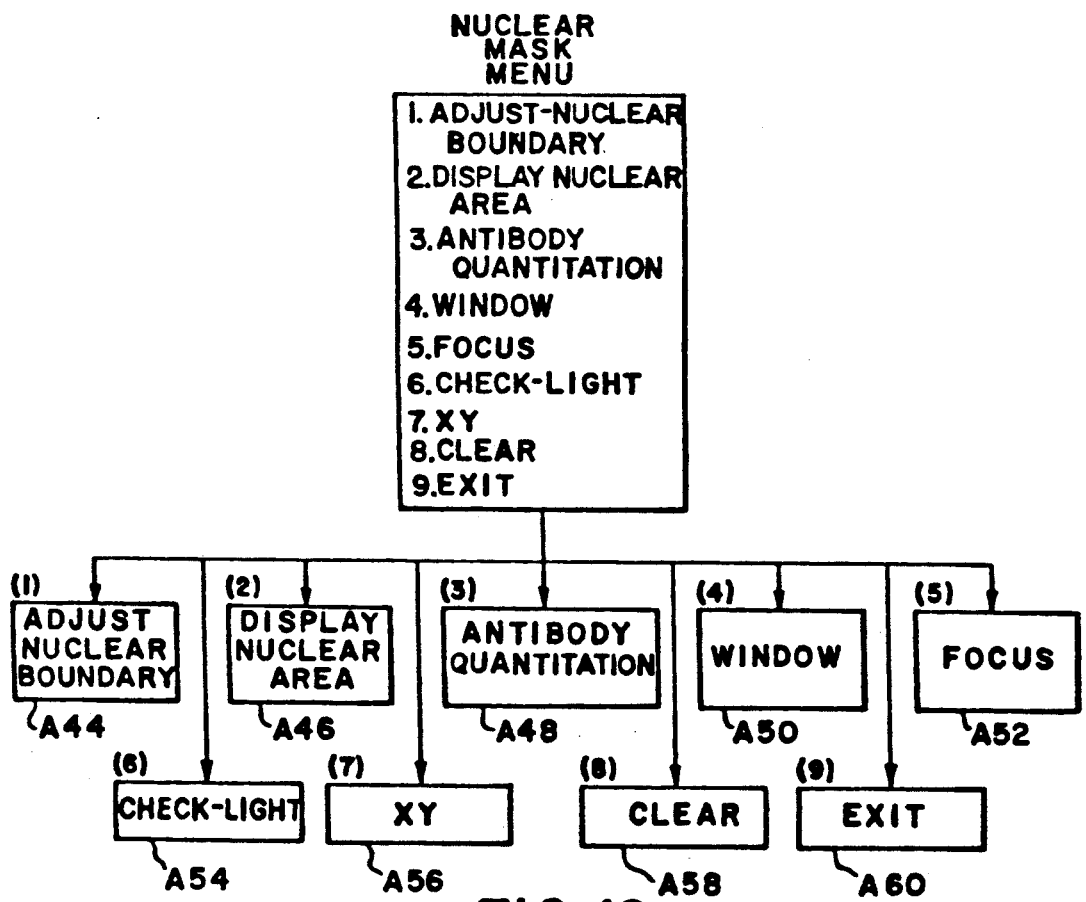
FIG. 19 is a functional flow chart of the nuclear mask menu of the nuclear mark screen illustrated in FIG. 12.
Figure 20:
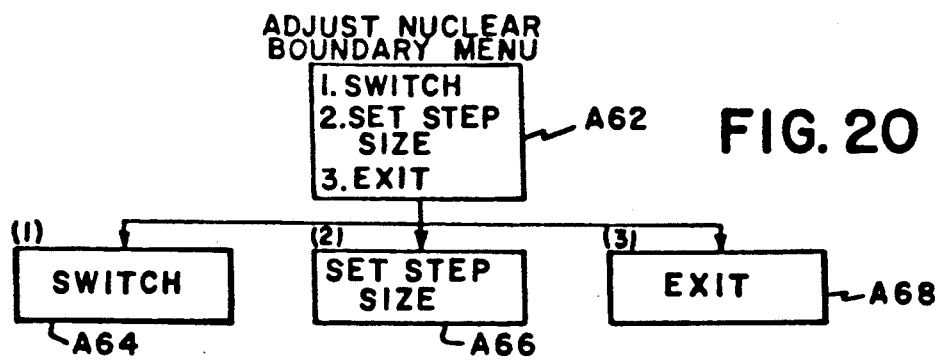
FIG. 20 is a functional flow chart of the adjust nuclear boundary menu of the adjust nuclear boundary screen illustrated in FIG. 12.

A description of the nuclear mask functions will now be more fully detailed with reference to FIG. 19. The adjust nuclear boundary function A44 will change the display on the monitor from the nuclear mask screen A16 to the adjust nuclear boundary screen A18. The adjust nuclear boundary screen A18 contains a menu for selection of the functions that allows an operator to change the nuclear boundary. The adjust nuclear boundary function must be used every time that the operator wants to measure data from an image field. Thus, every time a new image is selected for measurement, the adjust nuclear boundary function A44 must be selected and set before the display nuclear area function A46 or the antibody quantitation function A48 can be selected.

Selection of the display nuclear area function will cause the image monitor 37 to display the nuclear area on the screen. The program specifies a specific window in the image wherein the nuclear area in that specific window will be displayed in yellow and everything else in the image will be displayed in white. The yellow and white image will be cleared from monitor 37 whenever the next function is selected. This function gives a visual image for comparison with the calculation of nuclear area.

Selection of the antibody quantitation function A48 will cause the instruction monitor 62 to change the display from the nuclear mask screen A16 to the antibody quantitation screen A20. The antibody quantitation screen A20 illustrated in FIG. 16 contains a menu having functions that allow the user to measure an image, display a histogram of that data, smooth the histogram data, adjust the antibody boundary, change the histogram scale, clear the data, select the next image field, and to return to the label and calibration screen.

The selection of the window function A50 allows the operator to specify which areas of the current image to store for the mask image. The area which is to be stored can be shrunk, expanded or moved to a particular area in the field of interest. Initially, the window size is set to the whole image accept that part of the image which lies outside a window 64 (FIG. 1) displayed on the image monitor 37. The window function A50 allows the operator to adjust the size of window 68 and to move the window. When first entered, the window function A50 will be in a grow/shrink mode. While in this mode the operator is allowed to increase or decrease the window size. The following table lists the keys on keyboard 36 which the operator presses in order to change the window size:

| KEY | ACTION |
| --- | --- |
| 0 | alternate between large and small increments |
| 5 | alternate between the shrink and grow modes |
| 1 | increase or decrease the left and bottom sides of the window |
| 2 | increase or decrease the bottom side of the window |
| 3 | increase or decrease the right and bottom sides of the window |
| 4 | increase or decrease the left side of the window |
| 6 | increase or decrease the right side of the window |
| 7 | increase or decrease the left and top sides of the window |
| 8 | increase or decrease the top side of the window |

| KEY | ACTION |
|---|---|
| 9 | increase or decrease the right and top sides of the window |
| ESC | alternate between the grow/shrink mode and the move mode |

If the escape key is pressed by the operator while in the grow/shrink mode of the window function A50, the mode will change to a move mode. While in the move mode, the operator will be able to move the window anywhere within the field of view. The following table lists the keys that the operator can select to move the window:

| KEY | ACTION |
|---|---|
| 0 | alternate between large and small |
| 1 | move the window in the down-left direction |
| 2 | move the window in the down direction |
| 3 | move the window in the down-right direction |
| 4 | move the window in the left direction |
| 6 | move the window in the right direction |
| 7 | move the window in the up-left direction |
| 8 | move the window in the up direction |
| 9 | move the window in the up-right direction |
| ESC | alternate between the grow/shrink mode and the move mode |

If the operator wishes to adjust the window 68 for the current field of image, the window function must be selected before the adjust nuclear boundary function. The window size will be reset to normal every time the clear function A58 is selected in the nuclear mask screen, or when the antibody quantitation screen is exited.

The selection of the focus function A52 in the nuclear mask menu will provide color enhancement for the image on image monitor 37 so that the operator can perform more precise focusing of the image. The color enhanced image will disappear when any one of the following functions is selected: adjust nuclear boundary A44, display nuclear area A46, antibody quantitation A48, check light A54, focus A52, and window A50.

The check light function A54 will calculate the present average light level of the current field on the image monitor 37. If the light level is not the calibrated reference level between 129-131, the operator can return to the label calibrate screen to reset the level.

Selection of the xy function A56 for the nuclear mask screen A16 causes the x, y coordinates of the current image to be displayed. The xy function A56 displays the x, y coordinates of the current image relative to the origin which was set in the set-xy function A36 (FIG. 18). The coordinates will be continually displayed until the user presses another key. The xy function A56 is used to help locate fields of view which have previously been observed and marked for further analysis.

The selection of the clear function A58 will cause an erasure of all the image data stored for the session. The window size and placement will also be reset. After the clear function A50 has been selected by the operator, he will be requested to confirm the operation. To accept the confirmation, the operator selects the yes key and to reject the confirmation, the operator selects the no key or presses the escape key.

The exit function A60 in the nuclear mask screen A16 A16 will cause the instruction monitor 62 to change the display from the nuclear mask screen to the label/calibrate screen A14. Pressing the escape key is the same as selecting the exit function.

Figure 21:
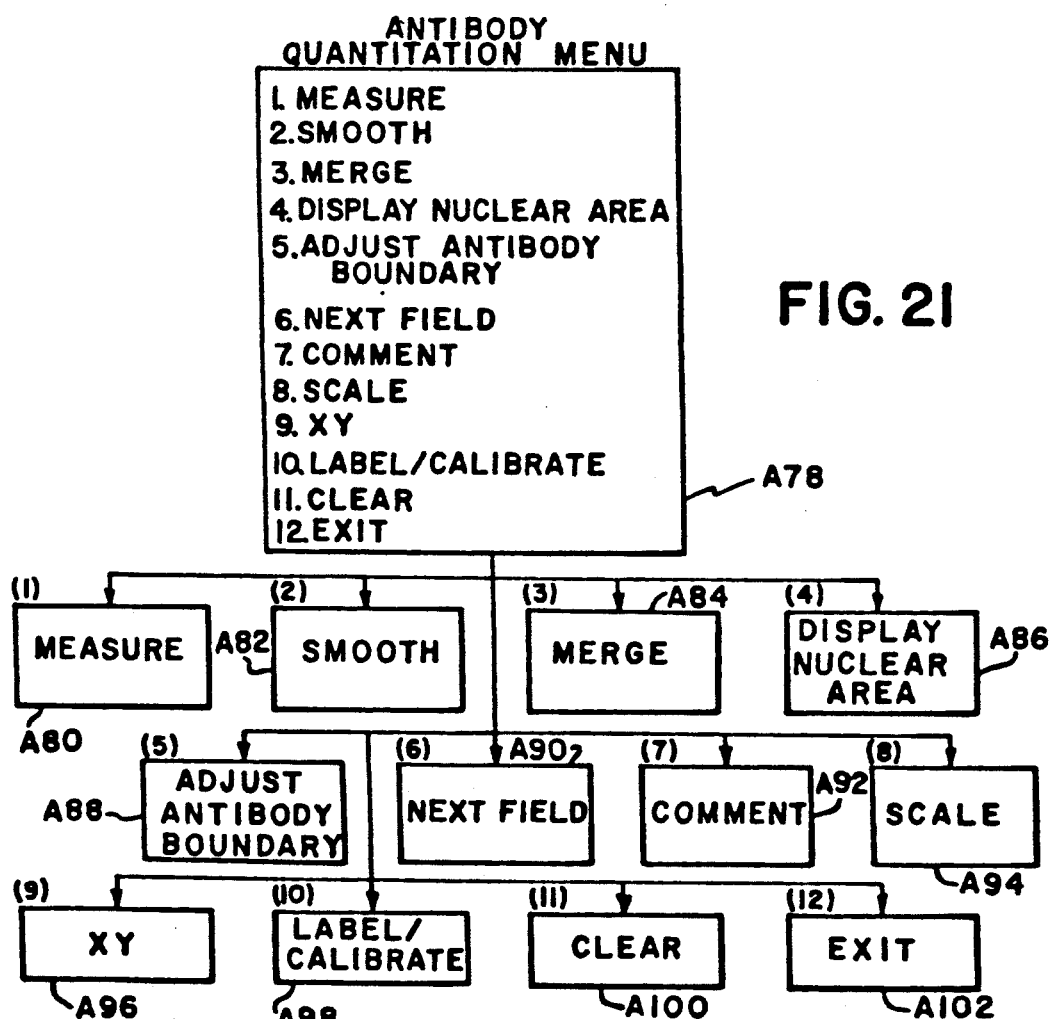
FIG. 21 is a functional flow chart of the antibody quantitation menu of the antibody quantitation screen illustrated in FIG. 12.

The functions of the antibody quantitation screen A20 will now be referenced to the antibody quantitation menu of FIG. 21. The selection of the measure function A80 allows the operator to measure the nuclear stain values that are inside of the window of the current field or image. After the first measure operation is completed, a histogram (FIG. 16) of the nuclear data of the measured image will be displayed on the antibody quantitation screen A20 of the instruction monitor 62 and the word "single" will appear on the bottom of the screen. The word single indicates to the operator that the displayed histogram belong to the image presently being measured. In addition, the positive percent, the nuclear area, and the positive stain intensity of the measured image is displayed. The measure function A80 can be selected by the operator any number of times for the current image as long as the merge function A84 has not been selected.

If the merge function A84 is selected, the measure function A80 will not longer apply just to the current image. The antibody quantitation screen A20 must be exited, and reentered in order to use the measure function A80 in the single mode again. If the measure function A80 is selected but the merge function A84 is not used to save the data, then the data that was calculated in the measure operation will be lost when the antibody quantitation screen A20 is exited.

Selection of the smooth function A82 allows the operator to smooth rough areas of the displayed histogram on the instruction monitor 62. The histogram can be smoothed to display from 1-9 peaks. After the smooth function A82 is selected, the cursor will move to the location on the screen A20 where the user can type in a smoothing value from keyboard 36. The smoothing value must be in the range 0-9. A smoothing value of zero will display the raw histogram on the screen while a smoothing value of 9 is the maximum amount of smoothing available. To execute the function and smooth the histogram, the operator presses the enter key after typing in the smoothing value. The operator can abort the smoothing operation before it is executed by pressing the escape key.

The selection of the merge function A84 allows the user to accumulate data from different specimen fields. The merge function A84 can only be selected after the measure function A80 has been used at least once for the current image. The merge function A84 will display in the histogram of all of the data that has been accumulated by the previous selections of the merge function A84. The scale of the histogram will be that of the measure function. The positive percent, nuclear area, and positive stain intensity of the accumulated data will also be displayed on the instruction monitor 62. The word total will be displayed at the bottom of the screen to indicate to the user that the displayed histogram represents all the data that was collected using the merge function A84.

The display nuclear area function A86 in the antibody quantitation screen A20 functions similar to that function described for the nuclear mask screen A16.

Selection of the adjust antibody boundary function A88 will change the display on the instruction monitor 62 from the antibody quantitation screen to the adjust antibody boundary screen A22. The adjust antibody boundary screen A22 provides a function that will allow the user to adjust the antibody boundary to a desired level.

Selection of the next field function A90 in the antibody quantitation screen A20 permits the operator to select another image to measure. The display on the instruction monitor 62 will change from the antibody quantitation screen A20 to the nuclear mask screen A16. Selection of this operation will also reset the window size.

When the operator selects the comment function A92, the apparatus 11 allows him to type in a comment on the antibody quantitation screen A20 in a particular area. The comment will appear only on the antibody quantitation screen. After the function is selected, the cursor will move to the location where the comment can be typed from keyboard 36. An editing routine is entered and the comment received. To exit the operation, the operator presses the enter or escape key. If the operator presses the enter key the system will save any changes that were made in the comment area. Otherwise, pressing the escape key will command the system to ignore any changes that were made to the comment area.

The scale function A94 allows the operator to change the scale on the horizontal axis of the histogram being displayed in the antibody quantitation screen A20. There are three scales to choose from, 0–47, 0–94, and 0–141 which represent the grey scale values of the pixels of the image. If the scale function A94 is selected when the current scale is 0–47, then the new scale will be 0–94. Similarly, if the scale function A94 is selected when the current scale is 0–94, then the new scale will be 0–141, etc. If the current scale is 0–47, then the last histogram column D will contain the histogram data for the grey scale values 48–255 and the first three columns A–C equally divides the rest of the scale. If the current scale is 0–94, then the last histogram column will contain the histogram data for the grey scale values 95–255. If the current grey scale is 0–141, then the last histogram column will contain histogram data for the grey scale values 142–255.

The selection of the xy function A96 will cause the system to display on the instruction monitor 62 the x, y coordinates of the current field or image. The xy function of this screen operates similarly to that described for the nuclear mask screen A16.

If the operator selects the label/calibrate function A98, the system will change the display from the antibody quantitation screen A20 to the label/calibrate screen A14. Selection of this function A98 will also reset the window size.

If the clear function A100 is selected by the operator, the system 13 will clear all the data presently acquired for the image and the window size will also be reset. After the clear function A100 has been selected, the operator will be requested to confirm the clear operation by a prompt on the instruction monitor 62. To accept the confirmation the operator will select the yes key and conversely, to reject the confirmation the operator will select the no key or press the escape key. If the yes key is selected by the operator, the display on the instruction monitor 62 will change from the antibody quantitation screen A20 to the nuclear mask screen A16.

Selection of the exit function A102 causes the system 13 to change the display on the instruction monitor 62 from the antibody quantitation screen A20 to the nuclear mask screen A16. Pressing the escape key is the same as selecting the exit function A102. The window size will also be reset upon the execution of the exit function A102.

Figure 22:
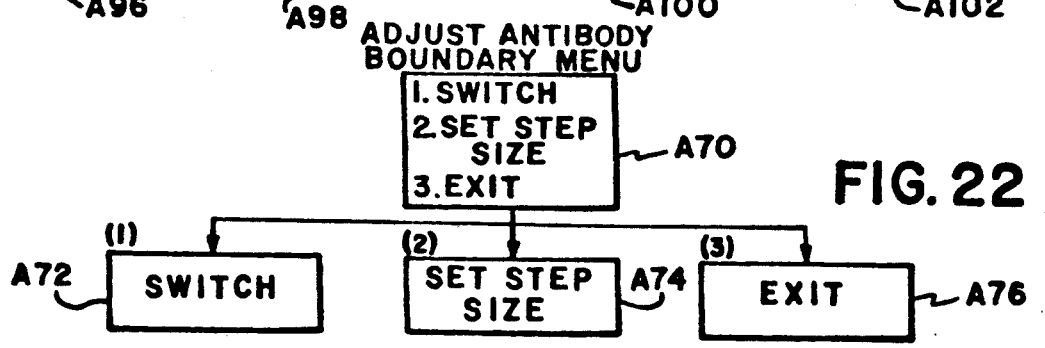
FIG. 22 is a functional flow chart of the adjust antibody boundary menu of the adjust antibody boundary screen illustrated in FIG. 12.

The functions available for the adjust antibody boundary screen A22 will now be more fully described with reference to the menu of FIG. 22. Selection of the switch function A72 will cause the image displayed on the image monitor 37 to alternate between a color enhanced image and the original image. However, image color enhancement, the focus function A52 (FIG. 19) must previously have been selected.

The set step size function A74 allows the operator to change the amount of grey scale units that the antibody boundary will change when one of the cursor keys is selected. The value chosen must be in the range of 0–128. After the set step size function A74 is selected, the cursor will move to the location on the adjust antibody boundary screen where the user can type in the new step size value. To exit from the set step size function A74, the operator presses either the enter or the escape keys. Pressing the enter key will save the step size change, while pressing the escape key will ignore any change that was made. As a default value the program initially sets the step size value equal to one.

Thereafter, repetitions of an up arrow key will increase the antibody boundary by the value of the step size for each press and the field under consideration with changed antibody boundary value will be displayed on the image monitor 37. Selection of the down arrow key will decrease the antibody boundary value by the value of the step size for each press. The new antibody boundary value will be displayed on the instruction monitor 62. Further, the image of the field on the monitor 37 will reflect the changes made in the boundary value.

Selection of the exit function A76 changes the display from the adjust antibody boundary screen A22 to the antibody quantitation screen A20. Pressing the escape key is the same as selecting the exit function.

FIG. 15 illustrates the report generation stage of the analysis which takes the form of a histogram. The histogram has as its ordinate axis the percentage of total nuclear area and as its abscissa axis the intensity of the stain. Thus, each bar of the histogram illustrates the percentage of the total nuclear area that was measured for a particular stain intensity. The stain intensity axis is divided up into four separate areas A–D with each having a greater of the stain intensity values, for example, area A corresponds to intensity values 0–64, area B corresponds to intensity values 65–128, area C to values between 129–192, and area D to values between 193–256. The sum of the percentage of total nuclear area for the stain intensities of each block A–D is displayed centered in the block. Further, a vertical marker is used to visually differentiate positive stain values from negative stain values.

A summary of the measurements made are displayed in the measurement report area next to their titles. The "measure count" indicates how many specimen fields have been measured to obtain the present data. The "positive percent" indicates the total percentage of nuclear area with positive stain, i.e., that area pictured right of the vertical marker in the histogram. The "nuclear area" is the total nuclear area of all the fields measured for the present data and is given in $\mu m^2$. The "positive stain intensity" is the average grey scale value arrived at taking into account all values of intensity for the positive stain values.

While a preferred embodiment of the invention has been illustrated, it will be obvious to those skilled of the art that various modifications and changes may be made thereto without departing from the spirit and scope of the invention as defined in the appended claims.

What is claimed is:

1. An apparatus for quantitation of nuclear antigen in a cell population which has been enhanced with an optical enhancement factor specific to a nuclear antigen such that the optical density of the optical enhancement factor relates to the location and nuclear antigen content of the cell population, and which cell population has been optically enhanced with a spectral stain material specific to the nuclear area which optically enhances the nuclear area of said cell population, said apparatus comprising:

means for digitizing an optical image of said cell population into a digital image having a plurality of pixels with grey scale values of intensity;

means for identifying from the digital image the nuclear area of the cell population at a first wavelength which allows identification of substantially all of the enhanced nuclear area;

means for identifying from the digital image the portions of said nuclear area optically enhanced specific to the nuclear antigen at second wavelength range which substantially excludes contribution from the spectral stain; and means for measuring from said digital image the optical density of said identified portion of said nuclear area which has been optically enhanced by the optical enhancement factor specific for the nuclear antigen.

2. An apparatus for the quantitation of estrogen receptors in a cell population as set forth in claim 1 wherein said means for measuring further includes:

means for averaging the stain intensity of the pixels of said identified portion of said nuclear area which is stained by said optical enhancement factor.

3. An apparatus for the quantitation of estrogen receptors in a cell population as set forth in claim 1 wherein said means for measuring further includes:

means for comparing the stain intensity of the pixels of said identified portion of said nuclear area which is stained by said optical enhancement factor with at least one other cellular population feature.

4. An apparatus for the quantitation of estrogen receptors in a cell population as set forth in claim 1 wherein:

said optical enhancement factor is an immunoperoxidase stain including a monoclonal antibody against estrophilin.

5. An apparatus for the quantitation of estrogen receptors in a cell population as set forth in claim 4 wherein said optical enhancement factor includes:

a counterstain specific to the nuclei of said cell population.

6. An apparatus for the quantitation of estrogen receptors in a cell population as set forth in claim 5 wherein said digitizing means includes:

first means for filtering said digital image such that said primary stain is enhanced relative to said counterstain.

7. An apparatus for the quantitation of estrogen receptors in a cell population as set forth in claim 5 wherein said digitizing means includes:

second means for filtering said digital image such that said counterstain is enhanced relative to said counterstain.

8. An apparatus for the quantitation of estrogen receptors in a cell population as set forth in claim 7 wherein:

said first filtering means produces a monochromatic image with a wavelength of approximately 650 nanometers.

9. An apparatus for the quantitation of estrogen receptors in a cell population as set forth in claim 8 wherein:

said second filtering means produces a monochromatic image with a wavelength of approximately 500 nanometers.

10. An image analysis apparatus for analyzing specimen cell objects on a slide which have been optically enhanced with a stain, said apparatus comprising:

processor means adapted to execute a control program which includes analysis functions for said cell objects:

image monitor means controlled by said processor means for displaying a digital image of said specimen cell objects;

instruction monitor means controlled by said processor means for displaying images of a plurality of instruction screens which provide for the selection of operations of said apparatus and input means controlled by said processor for communicating operator commands to said control program for selecting said analysis functions;

means for selectively filtering said image to enhance at least one feature of said cell objects relative to other features of said cell objects; and means, included in the control program means and selectable by said input means, for analyzing said filtered image.

11. An image analysis apparatus as set forth in claim 10 wherein:

said cell objects are human cells.

12. An image analysis apparatus as set forth in claim 11 wherein:

said slide is divided into a specimen cell section and a control section.

13. An image analysis apparatus as defined in claim 12 wherein:

said stain includes an antibody specific to said cell feature which is bound to an optical enhancement factor;

said antibody binding to said cell feature in amounts related to the quantity of said cell feature and its distribution in said cells such that said optical enhancement factor corresponds to said feature quantity by its optical density and to said feature distribution by its optical distribution.

14. An image analysis apparatus as defined in claim 13 wherein: against estrophilin; and said optical enhancement factor is peroxidase-antiperoxidase complex bound to said monoclonal antibody through a bridging antibody and activated to release a DAB precipitate.

15. An image analysis apparatus as defined in claim 14 wherein said filtering means include:

means for filtering said image in a narrow bandwidth around a first wavelength to produce a first filtered image; and means for filtering said image in a narrow bandwidth around a second wavelength to produce a second filtered image.

16. An image analysis apparatus as defined in claim 15 wherein:
   said first filtering means enhances the nucleus of said cells; and
   said second filtering means enhances those areas in a cell nucleus which includes DAB precipitate.

17. An image analysis apparatus as defined in claim 15 wherein:
   said cells are counterstained with methyl green to optically enhance the nucleus of each.

18. An image analysis apparatus as defined in claim 15 wherein:
   said first wavelength is 500 nanometers;
   said second wavelength is 650 nanometers.

19. An image analysis apparatus as defined in claim 18 wherein said analyzing means includes:
   means for analyzing said first filtered
   means for analyzing said second filtered image; and
   means for combining the analysis of said first and second filtered image into a combination analysis.

20. An image analysis apparatus as defined in claim 10 which further includes:
   mask means, included in said control program means and selectable by said input means, for controlling the display of the nuclear area on said image monitor from said first filtered image and for displaying a nuclear mask screen on said instruction monitor to inform the operator of the selection and image display.

21. An image analysis apparatus as defined in claim 20 which further includes:
   antibody means, included in said control program and selectable by said input means, for controlling the display of the stained area on said image monitor from said second filtered image and for displaying an antibody quantitation screen on said instruction monitor to inform the operator of the selection and image display.

22. An image analysis apparatus as defined in claim 20 which further includes:
   mask boundary means, included in said control program and selectable by said input means, for controlling the display of the nuclear area on said image monitor from pixel value of said first filtered image above a nuclear boundary threshold, and for interactively setting said nuclear boundary threshold.

23. An image analysis apparatus as defined in claim 21 which further includes:
   antibody boundary means, included in said control program and selectable by said input means, for controlling the display of the stained area in said image monitor from pixel values of said second filtered image above an antibody boundary level, and for interactively setting said antibody boundary 24. An image analysis apparatus as defined in claim 11 which further includes:
   calibration means, included in said control program and selectable by said input means, for interactively setting a reference level for said light source.

25. An image analysis apparatus as defined in claim 24 wherein said calibration means further includes:
   labeling means for interactively labeling the images of said cell objects.

* * * * *